US011817180B2

(12) United States Patent
Zhang et al.

(10) Patent No.: US 11,817,180 B2
(45) Date of Patent: Nov. 14, 2023

(54) SYSTEMS AND METHODS FOR ANALYZING NUCLEIC ACID SEQUENCES

(71) Applicant: LIFE TECHNOLOGIES CORPORATION, Carlsbad, CA (US)

(72) Inventors: Zheng Zhang, Pasadena, CA (US); Danwei Guo, San Mateo, CA (US); Yuandan Lou, Cupertino, CA (US); Asim Siddiqui, San Francisco, CA (US); Dumitru Brinza, San Mateo, CA (US)

(73) Assignee: Life Technologies Corporation, Carlsbad, CA (US)

( * ) Notice: Subject to any disclaimer, the term of this patent is extended or adjusted under 35 U.S.C. 154(b) by 996 days.

(21) Appl. No.: 16/279,315

(22) Filed: Feb. 19, 2019

(65) Prior Publication Data

US 2020/0051663 A1 Feb. 13, 2020

Related U.S. Application Data

(63) Continuation of application No. 13/097,677, filed on Apr. 29, 2011, now abandoned.

(60) Provisional application No. 61/406,543, filed on Oct. 25, 2010, provisional application No. 61/330,090, filed on Apr. 30, 2010.

(51) Int. Cl.
*G16B 30/10* (2019.01)
*G16B 30/00* (2019.01)
*G16B 30/20* (2019.01)

(52) U.S. Cl.
CPC ............ *G16B 30/10* (2019.02); *G16B 30/00* (2019.02); *G16B 30/20* (2019.02)

(58) Field of Classification Search
CPC ......... G16B 30/10; G16B 30/00; G16B 30/20
See application file for complete search history.

(56) References Cited

U.S. PATENT DOCUMENTS

| | | | |
|---|---|---|---|
| 5,430,886 A | 7/1995 | Furtek | |
| 5,504,931 A | 4/1996 | Furtek | |
| 5,577,249 A | 11/1996 | Califano | |
| 5,598,350 A | 1/1997 | Kawanishi et al. | |
| 5,601,982 A | 2/1997 | Sargent et al. | |
| 5,604,100 A | 2/1997 | Perlin | |
| 5,671,090 A | 9/1997 | Pernick et al. | |
| 5,706,498 A | 1/1998 | Fujimiya et al. | |
| 5,856,928 A | 1/1999 | Yan | |
| 5,873,052 A | 2/1999 | Sharaf | |
| 5,891,632 A | 4/1999 | Imai | |
| 5,964,860 A | 10/1999 | Peterson et al. | |
| 5,966,711 A | 10/1999 | Adams | |
| 6,001,562 A | 12/1999 | Milosavljevic | |
| 6,054,276 A | 4/2000 | Macevicz | |
| 6,068,977 A | 5/2000 | Perlin | |
| 6,117,634 A | 9/2000 | Langmore et al. | |
| 6,119,120 A | 9/2000 | Miller | |
| 6,143,498 A | 11/2000 | Olsen et al. | |
| 6,189,013 B1 | 2/2001 | Maslyn et al. | |
| 6,223,127 B1 | 4/2001 | Berno | |
| 6,223,128 B1 | 4/2001 | Allex et al. | |
| 6,223,175 B1 | 4/2001 | George et al. | |
| 6,223,186 B1 | 4/2001 | Rigault et al. | |
| 6,287,773 B1 | 9/2001 | Newell | |
| 6,363,399 B1 | 3/2002 | Maslyn et al. | |
| 6,383,743 B1 | 5/2002 | Kinzler et al. | |
| 6,389,428 B1 | 5/2002 | Rigault et al. | |
| 6,401,043 B1 | 6/2002 | Stanton, Jr. et al. | |
| 6,404,907 B1 | 6/2002 | Gilchrist et al. | |
| 6,421,613 B1 | 7/2002 | Nadimpalli et al. | |
| 6,470,277 B1 | 10/2002 | Chin et al. | |
| 6,484,105 B2 | 11/2002 | Zhang | |
| 6,505,126 B1 | 1/2003 | Hare et al. | |
| 6,714,874 B1 | 3/2004 | Myers et al. | |
| 6,785,614 B1 | 8/2004 | Collins et al. | |
| 6,895,337 B1 | 5/2005 | Scholl et al. | |
| 6,960,471 B2 | 11/2005 | Pecker et al. | |
| 6,961,664 B2 | 11/2005 | Selifonov et al. | |
| 6,963,865 B2 | 11/2005 | Bera | |
| 6,983,274 B2 | 1/2006 | Patzer | |
| 6,988,039 B2 | 1/2006 | Poleksic | |
| 6,990,238 B1 | 1/2006 | Saffer et al. | |
| 6,994,965 B2 | 2/2006 | Tamura et al. | |
| 6,996,474 B1 | 2/2006 | Colinge et al. | |

(Continued)

OTHER PUBLICATIONS

Lancaster, Joseph, Jeremy Buhler, and Roger D. Chamberlain. "Acceleration of ungapped extension in Mercury Blast." Microprocessors and microsystems 33.4 (2009): 281-289. (Year: 2009).*
Shendure, Jay, and Hanlee Ji. "Next-generation DNA sequencing." Nature biotechnology 26.10 (2008): 1135-1145. (Year: 2008).*
Lancaster et al. Acceleration of ungapped extension in Mercury BLAST Microprocessors and Microsystems vol. 33, 281-289—2009.

(Continued)

*Primary Examiner* — G. Steven Vanni
*Assistant Examiner* — Samantha J. Bowen

(57) ABSTRACT

Nucleic acid sequence mapping/assembly methods are disclosed. The methods initially map only a contiguous portion of each read to a reference sequence and then extends the mapping of the read at both ends of the mapped contiguous portion until the entire read is mapped (aligned). In various embodiments, a mapping score can be calculated for the read alignment using a scoring function, score $(i, j) = M + mx$, where M can be the number of matches in the extended alignment, x can be the number of mismatches in the alignment, and m can be a negative penalty for each mismatch. The mapping score can be utilized to rank or choose the best alignment for each read.

20 Claims, 15 Drawing Sheets

(56) References Cited

U.S. PATENT DOCUMENTS

| | | |
|---|---|---|
| 6,996,477 B2 | 2/2006 | Meyerson |
| 7,006,924 B2 | 2/2006 | Watanabe et al. |
| 7,007,001 B2 | 2/2006 | Oliver et al. |
| 7,039,238 B2 | 5/2006 | Sonmez et al. |
| 7,041,455 B2 | 5/2006 | Magness et al. |
| 7,043,371 B2 | 5/2006 | Wheeler |
| 7,054,755 B2 | 5/2006 | O'Reilly et al. |
| 7,058,634 B2 | 6/2006 | Potts et al. |
| 7,061,491 B2 | 6/2006 | Happel |
| 7,065,451 B2 | 6/2006 | Garner et al. |
| 7,078,504 B2 | 7/2006 | Short et al. |
| 7,085,651 B2 | 8/2006 | Yasuda et al. |
| 7,085,652 B2 | 8/2006 | Scaf et al. |
| 7,099,777 B1 | 8/2006 | Ghandour |
| 7,125,662 B2 | 10/2006 | Hall et al. |
| 7,133,781 B2 | 11/2006 | Toll et al. |
| 7,141,418 B2 | 11/2006 | Kunsch et al. |
| 7,181,373 B2 | 2/2007 | Le et al. |
| 7,205,111 B2 | 4/2007 | Christensen et al. |
| 7,217,509 B2 | 5/2007 | Wolffe et al. |
| 7,231,390 B2 | 6/2007 | Blair et al. |
| 7,254,489 B2 | 8/2007 | Mossel |
| 7,263,444 B2 | 8/2007 | Clark |
| 7,313,555 B2 | 12/2007 | Klier |
| 7,325,013 B2 | 1/2008 | Caruso |
| 7,328,111 B2 | 2/2008 | Porikli |
| 7,333,980 B2 | 2/2008 | Bjornson et al. |
| 7,365,164 B2 | 4/2008 | Nakao et al. |
| 7,386,523 B2 | 6/2008 | Diao |
| 7,396,646 B2 | 7/2008 | Quinlan et al. |
| 7,400,980 B2 | 7/2008 | Liu et al. |
| 7,424,369 B2 | 9/2008 | Braun et al. |
| 7,424,371 B2 | 9/2008 | Kamentsky |
| 7,424,464 B2 | 9/2008 | Oliver et al. |
| 7,444,243 B2 | 10/2008 | Mcininch |
| 7,451,123 B2 | 11/2008 | Platt et al. |
| 7,474,759 B2 | 1/2009 | Sternberg et al. |
| 7,475,087 B1 | 1/2009 | Lazo et al. |
| 7,512,498 B2 | 3/2009 | Pentkovski |
| 7,539,579 B2 | 5/2009 | Beattie et al. |
| 7,584,058 B2 | 9/2009 | Zabeau et al. |
| 7,590,291 B2 | 9/2009 | Bradski |
| 7,593,818 B2 | 9/2009 | Zabeau et al. |
| 7,599,802 B2 | 10/2009 | Harwood et al. |
| 7,604,998 B2 | 10/2009 | Elliott |
| 7,606,403 B2 | 10/2009 | Haussecker et al. |
| 7,614,036 B2 | 11/2009 | Bjornson et al. |
| 7,627,537 B2 | 12/2009 | Lai |
| 7,657,382 B2 | 2/2010 | Kwon et al. |
| 7,680,601 B1 | 3/2010 | Khosla et al. |
| 7,680,790 B2 | 3/2010 | Indeck et al. |
| 7,689,366 B2 | 3/2010 | Duck et al. |
| 7,689,638 B2 | 3/2010 | Theimer et al. |
| 7,700,284 B2 | 4/2010 | Romanov et al. |
| 7,702,595 B2 | 4/2010 | Shibuya |
| 7,702,610 B2 | 4/2010 | Zane et al. |
| 7,711,491 B2 | 5/2010 | Vandersall et al. |
| 7,734,427 B2 | 6/2010 | Clark |
| 7,747,641 B2 | 6/2010 | Kim et al. |
| 7,756,847 B2 | 7/2010 | Pauws et al. |
| 7,761,462 B2 | 7/2010 | Bjornson et al. |
| 7,769,708 B2 | 8/2010 | Caruso |
| 7,788,043 B2 | 8/2010 | Gill et al. |
| 7,788,279 B2 | 8/2010 | Mohajer et al. |
| 7,792,894 B1 | 9/2010 | Cohn et al. |
| 7,801,591 B1 | 9/2010 | Shusterman |
| 7,805,254 B2 | 9/2010 | Clark |
| 7,805,460 B2 | 9/2010 | Artan et al. |
| 7,807,375 B2 | 10/2010 | Cantor et al. |
| 7,809,509 B2 | 10/2010 | Milosavljevic |
| 7,809,510 B2 | 10/2010 | Milosavljevic |
| 7,822,782 B2 | 10/2010 | Chakravarty et al. |
| 7,831,392 B2 | 11/2010 | Antoniotti et al. |
| 7,853,410 B2 | 12/2010 | Selifonov et al. |
| 7,855,080 B2 | 12/2010 | Elliott |
| 7,856,322 B2 | 12/2010 | Kim et al. |
| 7,856,409 B2 | 12/2010 | Shibuya |
| 2003/0120429 A1* | 6/2003 | Li .................. G16B 30/10 702/19 |
| 2009/0318310 A1 | 12/2009 | Liu et al. |

OTHER PUBLICATIONS

Shendure et al., "Next-generation DNA sequencing", Nature Biotechnology, vol. 26, No. 10, Oct. 2008, pp. 1135-1145.

Li, H. et al., "Mapping short DNA sequencing reads and calling variants using mapping quality scores", Genome Research, vol. 18, Aug. 19, 2008, 1851-1858.

* cited by examiner

SYSTEMS AND METHODS FOR ANALYZING NUCLEIC ACID SEQUENCES

CROSS-REFERENCE TO RELATED APPLICATIONS

This application is a continuation of U.S. patent application Ser. No. 13/097,677, filed Apr. 29, 2011, which claims priority pursuant to 35 U.S.C. § 119(e) to U.S. Provisional Patent Application Ser. No. 61/330,090, entitled "Systems and Methods for Mapping DNA Sequence Reads," filed on Apr. 30, 2010, and to U.S. Provisional Patent Application Ser. No. 61/406,543, entitled "Systems and Methods for Mapping DNA Sequence Reads," filed on Oct. 25, 2010, each of which is incorporated by reference herein in its entirety.

FIELD

The present disclosure generally relates to the field of nucleic acid sequencing including systems and methods for reconstructing large continuous genome sequences (e.g., contigs) from fragment sequence reads.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible for sequencing. These goals can be reached through the use of sequencing platforms and methods that provide sample preparation for larger quantities of samples of significant complexity, sequencing larger numbers of complex samples, and/or a high volume of information generation and analysis in a short period of time. Various methods, such as, for example, sequencing by synthesis, sequencing by hybridization, and sequencing by ligation are evolving to meet these challenges.

Research into fast and efficient nucleic acid (e.g., genome, exome, etc.) sequence assembly methods is vital to the sequencing industry as NGS technologies can provide ultra-high throughput nucleic acid sequencing. As such sequencing systems incorporating NGS technologies can produce a large number of short sequence reads in a relatively short amount time. Sequence assembly methods must be able to assemble and/or map a large number of reads quickly and efficiently (i.e., minimize use of computational resources). For example, the sequencing of a human size genome can result in tens or hundreds of millions of reads that need to be assembled before they can be further analyzed to determine their biological, diagnostic and/or therapeutic relevance.

Sequence assembly can generally be divided into two broad categories: de novo assembly and reference genome mapping assembly. In de novo assembly, sequence reads are assembled together so that they form a new and previously unknown sequence. Whereas in reference genome mapping, sequence reads are assembled against an existing backbone sequence (e.g., reference sequence, etc.) to build a sequence that is similar but not necessarily identical to the backbone sequence.

Once a backbone sequence is found for an organism, comparative sequencing or resequencing can be used to characterize the genetic diversity within the organism's species or between closely related species.

SUMMARY

Systems, methods, software and computer-usable media for reconstructing larger continuous biomolecule-related sequences (e.g., contigs, exomes, genomes, etc.) from smaller biomolecule-related sequence reads are disclosed. Biomolecule-related sequences can relate to proteins, peptides, nucleic acids, and the like, and can include structural and functional information such as secondary or tertiary structures, amino acid or nucleotide sequences, sequence motifs, binding properties, genetic mutations and variants, and the like.

Using nucleic acids as an example, in various embodiments, smaller nucleic acid sequence reads can be assembled into larger sequences using an anchor-extension mapping method that initially maps (aligns) only a contiguous portion of each read to a reference sequence and then extends the mapping of the read at both ends of the mapped contiguous portion until the entire read is mapped (aligned). In various embodiments, a mapping score can be calculated for the read alignment using a scoring function, score $(i, j)=M+mx$, where M can be the number of matches in the extended alignment, x can be the number of mismatches in the alignment, and m can be a negative penalty for each mismatch. In various embodiments, the negative penalty, m, for each mismatch is user defined. In various embodiments, the negative penalty, m, for each mismatch is automatically determined by the algorithm/script/program implementing the anchor-extension mapping method to maximize the accuracy of the read alignment.

In various embodiments, the nucleic acid sequence read data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

In one aspect, a system for implementing an anchor-extension mapping method can include a first data store (for storing nucleic acid sequencing data), a second data store (for storing reference sequence data) and a computing device (hosting a mapping module) in communication with the first data store and the second data store, is disclosed. In various embodiments, the computing device can be a workstation, mainframe computer, personal computer, mobile device, etc.

In various embodiments, the mapping module can be configured to: obtain a nucleic acid sequence read from the first data store, obtain a reference sequence from the second data store, select a contiguous portion of the nucleic acid sequence read, map the contiguous portion of the nucleic acid sequence read to the reference sequence using an approximate string mapping method that allows for a set number of mismatches between the contiguous portion and the reference sequence and produces at least one match of the contiguous portion to the reference sequence, and map a remaining portion of the nucleic acid sequence read to the reference sequence using an ungapped local alignment method that produces an alignment of the remaining portion extending from the at least one match to complete a map of the nucleic acid sequence read to the reference sequence.

In one aspect, a system for assembling a nucleic acid sequence from a plurality of paired sequence reads can include a first data store and a computing device in communications with the first data store, is disclosed. In various embodiments, the computing device can be a workstation, mainframe computer, personal computer, mobile device, etc.

In various embodiments, the first data store can be configured to store the plurality of paired sequence reads, wherein each of the plurality of paired sequence reads comprise a pair of pairwise sequences separated by an intervening length.

In various embodiments the computing device can host a first assembly module and a second assembly module. The first assembly module can be configured to assemble the plurality of paired sequence reads to form a scaffold of the nucleic acid sequence wherein the scaffold comprises a plurality of contiguous sequences separated by a gap region and wherein each of the plurality of contiguous sequences is comprised of two or more paired sequence reads. The second assembly module can be configured to assemble hanging pairwise sequences of the assembled paired sequence reads to fill in the gap region.

These and other features are provided herein.

DRAWINGS

For a more complete understanding of the principles disclosed herein, and the advantages thereof, reference is now made to the following descriptions taken in conjunction with the accompanying drawings, in which.

Figure 1:
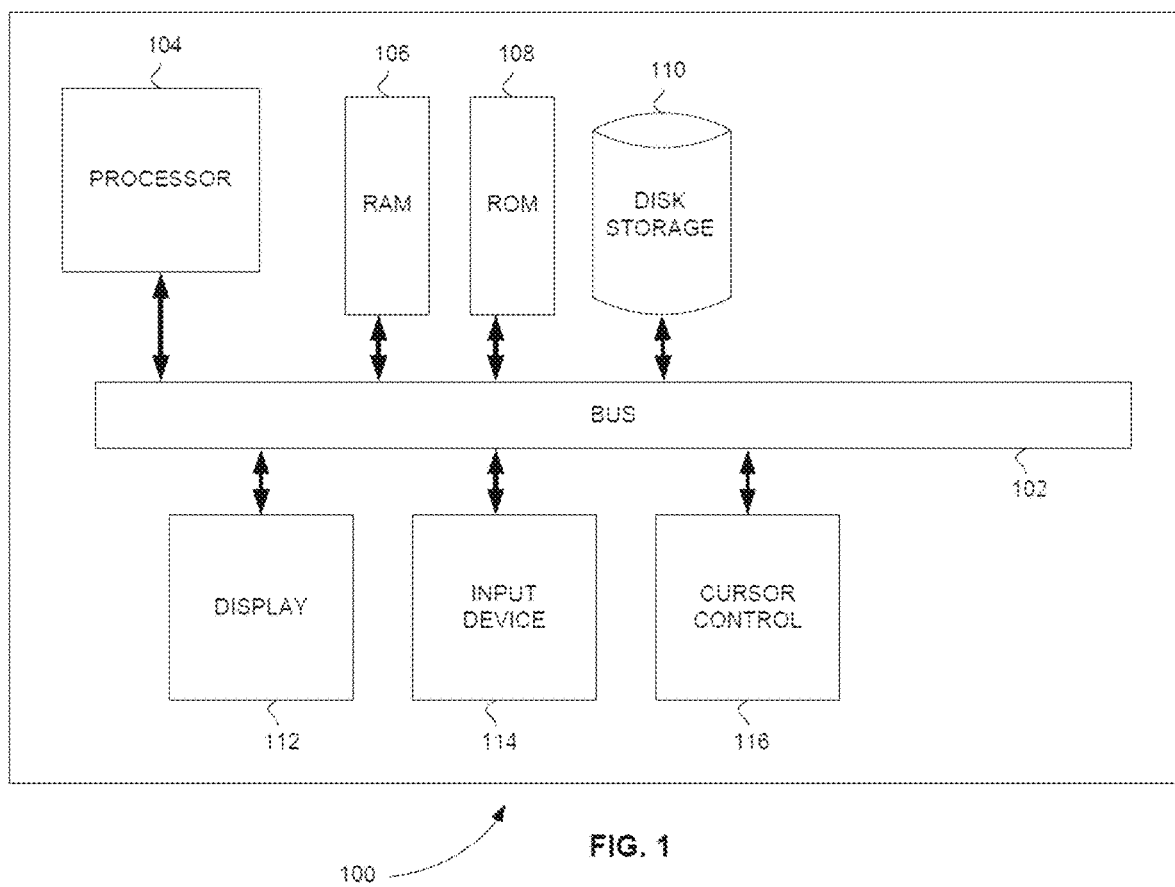
FIG. 1 is a block diagram that illustrates a computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for reconstructing larger continuous sequences (e.g., contigs) from smaller fragment sequence reads are described in this specification.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless defined otherwise, all technical and scientific terms used herein have the same meaning as is commonly understood by one of ordinary skill in the art to which the various embodiments described herein belongs. When definitions of terms in incorporated references appear to differ from the definitions provided in the present teachings, the definition provided in the present teachings shall control.

It will be appreciated that there is an implied "about" prior to the temperatures, concentrations, times, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

As used herein, "a" or "an" means "at least one" or "one or more."

A "system" denotes a set of components, real or abstract, comprising a whole where each component interacts with or is related to at least one other component within the whole.

A "biomolecule" is any molecule that is produced by a living organism, including large polymeric molecules such as proteins, polysaccharides, lipids, and nucleic acids as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the SOLiD Sequencing System of Life Technologies Corp. provides massively parallel sequencing with enhanced accuracy. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The phrase "sequencing run" refers to any step or portion of a sequencing experiment performed to determine some information relating to at least one biomolecule (e.g., nucleic acid molecule).

It is well known that DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. It is also known that all of these 5 types of nucleotides specifically bind to one another in combinations called complementary base pairing. That is, adenine (A) pairs with thymine (T) (in the case of RNA, however, adenine (A) pairs with uracil (U)), and cytosine (C) pairs with guanine (G), so that each of these base pairs forms a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

The phrase "ligation cycle" refers to a step in a sequence-by-ligation process where a probe sequence is ligated to a primer or another probe sequence.

The phrase "color call" refers to an observed dye color resulting from the detection of a probe sequence after a ligation cycle of a sequencing run.

The phrase "color space" refers to a nucleic acid sequence data schema where nucleic acid sequence information is represented by a set of colors (e.g., color calls, color signals, etc.) each carrying details about the identity and/or positional sequence of bases that comprise the nucleic acid sequence. For example, the nucleic acid sequence "ATCGA" can be represented in color space by various combinations of colors that are measured as the nucleic acid sequence is interrogated using optical detection-based (e.g., dye-based, etc.) sequencing techniques such as those employed by the SOLiD System. That is, in various embodiments, the SOLiD System can employ a schema that represents a nucleic acid fragment sequence as an initial base followed by a sequence of overlapping dimers (adjacent pairs of bases). The system can encode each dimer with one of four colors using a coding scheme that results in a sequence of color calls that represent a nucleotide sequence.

The phrase "base space" refers to a nucleic acid sequence data schema where nucleic acid sequence information is represented by the actual nucleotide base composition of the nucleic acid sequence. For example, the nucleic acid sequence "ATCGA" is represented in base space by the actual nucleotide base identities (e.g., A, T/or U, C, G) of the nucleic acid sequence.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'->3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The techniques of "paired-end," "pairwise," "paired tag," or "mate pair" sequencing are generally known in the art of molecular biology (Siegel A. F. et al., Genomics. 2000, 68: 237-246; Roach J. C. et al., Genomics. 1995, 26: 345-353). These sequencing techniques can allow the determination of multiple "reads" of sequence, each from a different place on a single polynucleotide. Typically, the distance between the two reads or other information regarding a relationship between the reads is known. In some situations, these sequencing techniques provide more information than does sequencing two stretches of nucleic acid sequences in a random fashion. With the use of appropriate software tools for the assembly of sequence information (e.g., Millikin S. C. et al., Genome Res. 2003, 13: 81-90; Kent, W. J. et al., Genome Res. 2001, 11: 1541-8) it is possible to make use of the knowledge that the "paired-end," "pairwise," "paired tag" or "mate pair" sequences are not completely random, but are known to occur a known distance apart and/or to have some other relationship, and are therefore linked or paired in the genome. This information can aid in the assembly of whole nucleic acid sequences into a consensus sequence.

Computer-Implemented System

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

Various forms of computer readable media can be involved in carrying one or more sequences of one or more instructions to processor 104 for execution. For example, the instructions can initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 can carry the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 11:
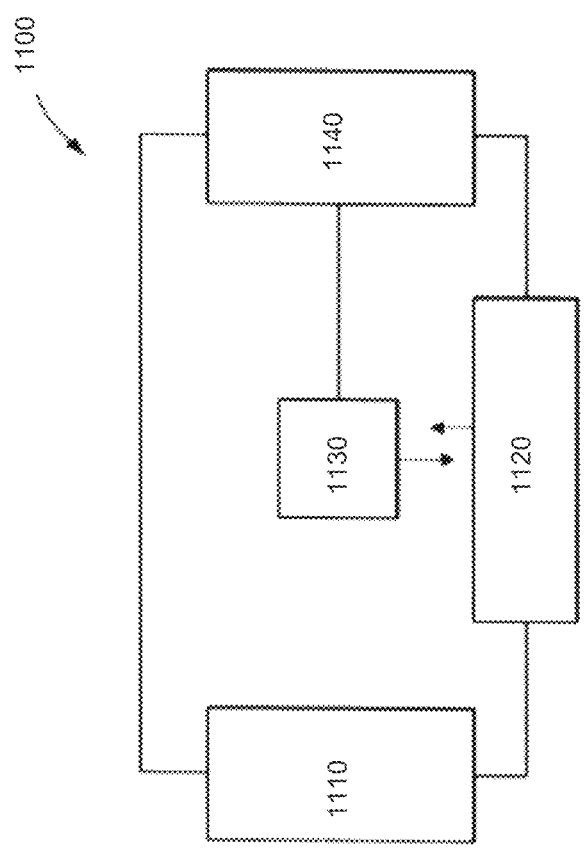
FIG. 11 is a block diagram of a nucleic acid sequencing platform, in accordance with various embodiments.

Various embodiments of nucleic acid sequencing platforms (i.e., nucleic acid sequencer) can include components as displayed in the block diagram of FIG. 11. According to various embodiments, sequencing instrument 1100 can include a fluidic delivery and control unit 1110, a sample processing unit 1120, a signal detection unit 1130, and a data acquisition, analysis and control unit 1140. Various embodiments of instrumentation, reagents, libraries and methods used for next generation sequencing are described in U.S. Patent Application Publication No. 2007/066931 (Ser. No. 11/737308) and U.S. Patent Application Publication No. 2008/003571 (Ser. No. 11/345,979) to McKernan, et al., which applications are incorporated herein by reference. Various embodiments of instrument 1100 can provide for automated sequencing that can be used to gather sequence information from a plurality of sequences in parallel, i.e., substantially simultaneously.

In various embodiments, the fluidics delivery and control unit 1110 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 1120 can include a sample chamber, such as flow cell, a substrate, a micro-array, a multi-well tray, or the like. The sample processing unit 1120 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 1130 can include an imaging or detection sensor. For example, the imaging or detection sensor can include a CCD, a CMOS, an ion sensor, such as an ion sensitive layer overlying a CMOS, a current detector, or the like. The signal detection unit 1130 can include an excitation system to cause a probe, such as a fluorescent dye, to emit a signal. The expectation system can include an illumination source, such as arc lamp, a laser, a light emitting diode (LED), or the like. In particular embodiments, the signal detection unit 1130 can include optics for the transmission of light from an illumination source to the sample or from the sample to the imaging or detection sensor. Alternatively, the signal detection unit 1130 may not include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, changes in an electrical current can be detected as a nucleic acid passes through a nanopore without the need for an illumination source.

In various embodiments, data acquisition analysis and control unit 1140 can monitor various system parameters. The system parameters can include temperature of various portions of instrument 1100, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 1100 can be used to practice variety of sequencing methods including ligation-based methods, sequencing by synthesis, single molecule methods, nanopore sequencing, and other sequencing techniques. Ligation sequencing can include single ligation techniques, or change ligation techniques where multiple ligation are performed in sequence on a single primary. Sequencing by synthesis can include the incorporation of dye labeled nucleotides, chain termination, ion/proton sequencing, pyrophosphate sequencing, or the like. Single molecule techniques can include continuous sequencing, where the identity of the nuclear type is determined during incorporation without the need to pause or delay the sequencing reaction, or staggered sequence, where the sequencing reactions is paused to determine the identity of the incorporated nucleotide.

In various embodiments, the sequencing instrument 1100 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 1100 can obtain the sequence information from a single nucleic acid molecule or from a group of substantially identical nucleic acid molecules.

In various embodiments, sequencing instrument 1100 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Nucleic Acid Assembly/Mapping Systems

Figure 2:
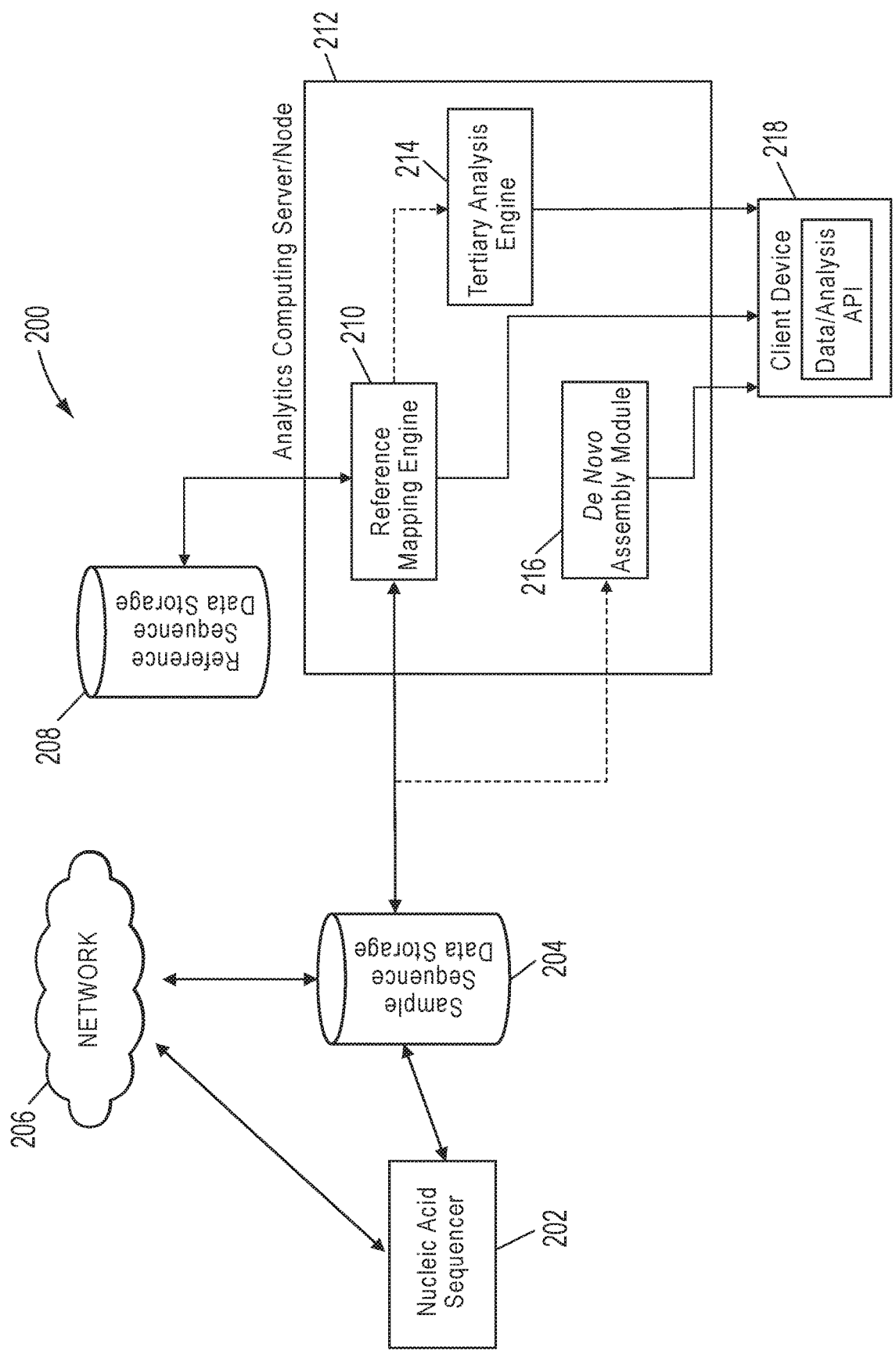
FIG. 2 is a schematic diagram of a system for reconstructing a nucleic acid sequence, in accordance with various embodiments.

FIG. 2 is a schematic diagram of a system 200 for reconstructing a nucleic acid sequence, in accordance with various embodiments. As shown herein, the system 200 can include a nucleic acid sequencer 202, a sample sequence data storage 204, a reference sequence data storage 208 and an analytics computing device/server/node 212. In various embodiments, the analytics computing device/server/node 212 can be a workstation, mainframe computer, personal computer, mobile device, etc.

The nucleic acid sequencer 202 can be configured to analyze (i.e., interrogate) a nucleic acid fragment (e.g., single fragment, mate-pair fragment, paired-end fragment, etc.) utilizing all available varieties of techniques, platforms or technologies to obtain nucleic acid sequence information. In various embodiments, the nucleic acid sequencer 202 can be in communications with the sample sequence data storage 204 either directly via a data cable (e.g., serial cable, direct cable connection, etc.) or bus linkage or, alternatively, through a network connection 206 (e.g., Internet, LAN, WAN, VPN, etc.). In various embodiments, the network connection 206 can be a "hardwired" physical connection. For example, the nucleic acid sequencer 202 can be communicatively connected (via Category 5 (CAT5), fiber optic or equivalent cabling) to a data server (not shown) that can be communicatively connected (via CAT5, fiber optic or equivalent cabling) through the Internet and to the sample sequence data storage 204. In various embodiments, the network connection can be a wireless network connection (e.g., Wi-Fi, WLAN, etc.). For example, utilizing an 802.11b/g or equivalent transmission format. In practice, the network connection utilized is dependent upon the particular requirements of the system 200. In various embodiments, the sample sequence data storage 204 can be an integrated part of the nucleic acid sequencer 202.

In various embodiments, the sample sequence data storage 204 can be any database storage device, system or implementation (e.g., data storage partition, etc.) that is configured to organize and store nucleic acid sequence read data generated by nucleic acid sequencer 202 such that the data can be searched and retrieved manually (i.e., by a database administrator/client operator) or automatically by way of a computer program/application/software script. In various embodiments, the reference data storage 208 can be any database device, storage system or implementation (e.g., data storage partition, etc.) that is configured to organize and store reference sequences (e.g., whole/partial genome, whole/partial exome, etc.) such that the data can be searched and retrieved manually (i.e., by a database administrator/client operator) or automatically by way of a computer program/application/software script. In various embodiments, the sample nucleic acid sequencing read data can be stored on the sample sequence data storage 204 and/or the reference data storage 208 in a variety of different data file types/formats, including, but not limited to: *.fasta, *.csfasta, *seq.txt, *qseq.txt, *.fastq, *.sff, *prb.txt, *.sms, *srs and/or *.qv.

In various embodiments, the sample sequence data storage 204 and the reference data storage 208 are independent standalone devices/systems or implemented on different devices. In various embodiments, the sample sequence data storage 204 and the reference data storage 208 are implemented on the same device/system. In various embodiments, the sample sequence data storage 204 and/or the reference data storage 208 can be implemented on the analytics computing device/server/node 212.

The analytics computing device/server/node 212 can be in communications with the sample sequence data storage 204 and the reference data storage 208 either directly via a data cable (e.g., serial cable, direct cable connection, etc.) or bus linkage or, alternatively, through a network connection (e.g., Internet, LAN, WAN, VPN, etc.). In various embodiments, analytics computing device/server/node 212 can host a reference mapping engine 210, a de novo mapping module 216 and/or a tertiary analysis engine 214. In various embodiments, the reference mapping engine 210 can be configured to obtain sample nucleic acid sequence reads from the sample data storage 204 and map them against one or more reference sequences obtained from the reference data storage 208 to assemble the reads into a sequence that is similar but not necessarily identical to the reference sequence using all varieties of reference mapping/alignment techniques and methods. The reassembled sequence can then be further analyzed by one or more optional tertiary analysis engines 214 to identify differences in the genetic makeup (genotype), gene expression or epigenetic status of individuals that can result in large differences in physical characteristics (phenotype). For example, in various embodiments, the tertiary analysis engine 214 can be configured to identify various genomic variants (in the assembled sequence) due to mutations, recombination/crossover or genetic drift. Examples of types of genomic variants include, but are not limited to: single nucleotide polymorphisms (SNPs), copy number variations (CNVs), insertions/deletions (Indels), inversions, etc.

The optional de novo mapping module 216 can be configured to assemble sample nucleic acid sequence reads from the sample data storage 204 into new and previously unknown sequences.

It should be understood, however, that the various engines and modules hosted on the analytics computing device/server/node 212 can be combined or collapsed into a single engine or module, depending on the requirements of the particular application or system architecture. Moreover, in various embodiments, the analytics computing device/server/node 212 can host additional engines or modules as needed by the particular application or system architecture.

In various embodiments, the mapping and/or tertiary analysis engines are configured to process the nucleic acid and/or reference sequence reads in color space. In various embodiments, the mapping and/or tertiary analysis engines are configured to process the nucleic acid and/or reference sequence reads in base space. It should be understood, however, that the mapping and/or tertiary analysis engines disclosed herein can process or analyze nucleic acid sequence data in any schema or format as long as the schema or format can convey the base identity and position of the nucleic acid sequence.

In various embodiments, the sample nucleic acid sequencing read and referenced sequence data can be supplied to the analytics computing device/server/node 212 in a variety of different input data file types/formats, including, but not limited to: *.fasta, *.csfasta, *seq.txt, *qseq.txt, *.fastq, *.sff, *prb.txt, *.sms, *srs and/or *.qv.

Client terminal 218 can be a thin client or thick client computing device. In various embodiments, client terminal 218 can have a web browser (e.g., INTERNET EXPLORER™, FIREFOX™, SAFARI™, etc) that can be used to control the operation of the reference mapping engine 210, the de novo mapping module 216 and/or the tertiary analysis engine 214. That is, the client terminal 218 can access the reference mapping engine 210, the de novo mapping module 216 and/or the tertiary analysis engine 214 using a browser to control their function. For example, the client terminal 218 can be used to configure the operating parameters (e.g., mismatch constraint, quality value thresholds, etc.) of the various engines, depending on the requirements of the particular application. Similarly, client terminal 110 can also display the results of the analysis performed by the reference mapping engine 210, the de novo mapping module 216 and/or the tertiary analysis engine 214.

Anchor-Extension Mapping

The wide adoption of high-throughput sequencing (i.e., NGS technologies) demands a fast and computationally efficient mapping tool that can map or align billions of short reads against large reference genomes of higher order organisms (e.g., humans, primates, fish, etc.). Currently, most of existing nucleic acid sequence read mapping tools solve an approximate string matching problem by allowing k number of mismatches. Hash and various implementation of suffix tree are the two main methods used. When read length increases, the error rate difference between the beginning and end of the reads can be fairly significant; which can require the mapping tool to allow for a large number of mismatches in order to achieve good sensitivity. This can slow down mapping significantly, especially for the suffix based methods, just when the overall throughput of nucleic acid sequencing technologies increases exponentially.

Embodiments of systems and methods for mapping a read of a nucleic acid sequence to a reference sequence are described herein. As described above, nucleic acid sequencing systems incorporating high-throughput sequencing technologies must be able to map a large number of sequence reads against a reference sequence (e.g., reference genome, etc.) quickly and efficiently.

In various embodiments, an anchor-extension method can be used to map a large number of reads against a reference sequence (e.g., genome, exome, etc.) in a short amount of time without requiring large numbers of mismatches as the read length is increased. In various embodiments, a predetermined portion (called an anchor region) of each read can be aligned to the reference sequence while allowing for a certain number of mismatches. When hits to the anchor region are found, an extension step can be executed to try to extend the alignment in (possibly) both directions to get a longer alignment. A hit is, for example, can be a match between the reference sequence and the anchor region that includes a minimum number of mismatches (i.e., conforms to a set mismatch constraint). In various embodiments, the mapping to the anchored region can be performed with an approximate string mapping technique. In various embodiments, the extension step can be performed with an ungapped local alignment technique.

Figure 3:
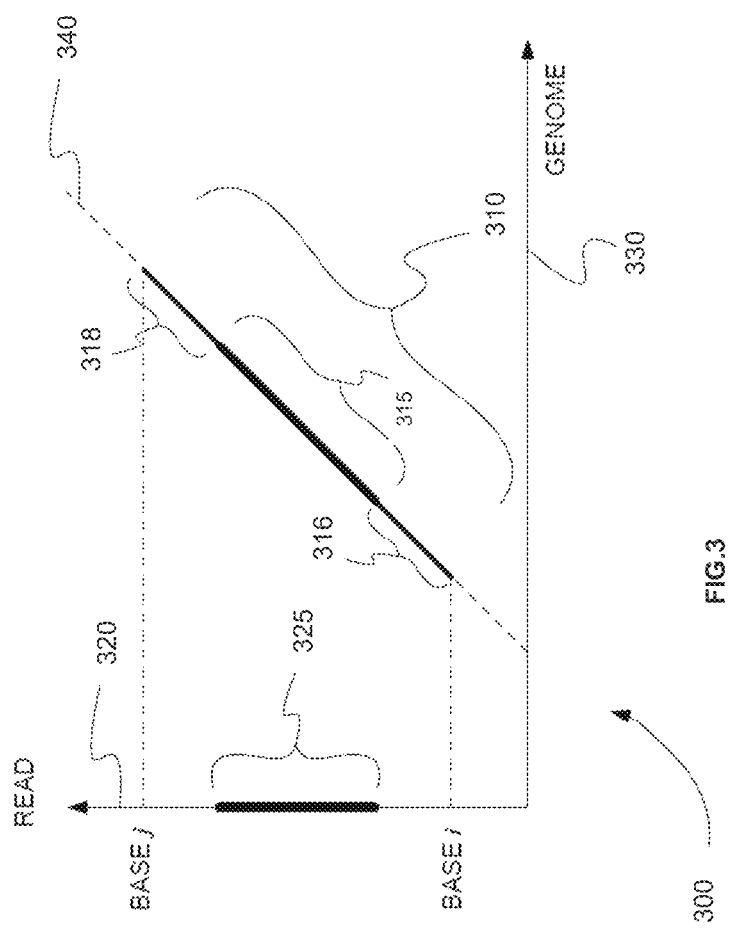
FIG. 3 is a diagram showing an alignment using an anchor-extension mapping method, in accordance with various embodiments.

FIG. 3 is a diagram 300 showing an alignment 310 using an anchor-extension mapping method, in accordance with various embodiments. As depicted herein, a nucleic acid sequence read 320 is shown along a vertical axis. A reference sequence 330 is shown along the horizontal axis. Read 320 can include an anchor region 325. A hit or match to the anchor region 325 is shown by anchor alignment 315. After a hit is found, the extension step can be performed for all the positions on alignment line 340. Read 320 and alignment line 340 can have the same length, for example. Alignment extensions to bases i and j of read 320 are shown by lines 316 and 318.

In various embodiments, for each pair of bases i and j, an alignment score can be calculated for the alignment extensions of the pair. That is, an alignment score can be calculated for each location on the reference sequence that the anchor region 325 maps to and extends. The location and corresponding alignment extensions with the best score can be chosen for the final alignment of the read 320. In various embodiments, the score of an extended alignment can be calculated using a scoring function, score (i, j)=M+mx, where M is the number of matches in the extended alignment, x is the number of mismatches in the alignment, and m is a negative penalty for each mismatch. In various embodiments, the negative penalty, m, for each mismatch is user defined. In various embodiments, the negative penalty, m, for each mismatch is automatically determined by the algorithm/script/program implementing the anchor-extension mapping method to maximize the accuracy of the read 320 alignment.

In various embodiments, according to the scoring function, each match can be given a score of one and each mismatch can be given a score of m. Therefore, the extension step calculates the score for all possible i and j and selects the extended alignment with the best score as the extended alignment that is reported. One skilled in the art will recognize that the extension step finds the best ungapped local alignment for each read.

Overall the anchor-extension mapping method can significantly improve mapping speed. For example, for a read 320 with a length of 50 bases, the error rate at the first 25 bases is typically low. Consequently, in various embodiments, the first 25 bases can be used as the anchor region and two mismatches can be allowed. An extended alignment mismatch can be given a mismatch penalty (m) of minus two, for example. Finding a hit to only the anchor region (as opposed to the entire length of the read 320) results in a significant improvement in the mapping speed, because finding matches using approximate string mapping accounts for more than 90 percent of the running time. For example, running approximate string mapping using a read length of 50 bases and allowing 6 mismatches can be five or more times slower than using a read length of 25 bases and allowing 2 mismatches.

In various embodiments, the anchor-extension mapping method can be performed using color space nucleic acid sequence data. In various embodiments, the anchor-extension mapping method can be performed using base space nucleic acid sequence data. It should be understood, however, that the anchor-extension method disclosed herein can be performed using any schema or format of nucleic acid sequence information as long as the schema or format can convey the base identity and position A single nucleotide polymorphism (SNP), however, can affect the performance of the anchor-extension mapping method. Because the method assumes that the bases in the anchor region are highly accurate, the presence of a SNP can affect the ability of the method to find a hit or match. This issue is magnified in certain nucleic acid sequencing systems where a sequence of color calls is used to represent a nucleotide sequence. As described above, some nucleic acid sequencing systems encode adjacent pairs of bases with a single color call. As a result, a single SNP can result in two sequence mismatches. Similarly, repetitive regions of a genome or reference sequence can also affect the performance of the anchor-extension mapping method. That is, a selected anchor can map to too many regions on the genome or reference sequence because the anchor region matches a sequence string that repeats on many different locations on the genome or reference sequence.

It should be understood, however, that the anchor-extension mapping method depicted in diagram 300 can also be applied to map biological sequences other than nucleic acid sequences or even non-biological sequences. For example, the anchor-extension mapping method can be applied to map a sample protein sequence (basically a sequence comprised of amino acids) against a reference protein sequence in proteomics research. Alternatively, the anchor-extension mapping method can also be applied to map natural language text (text strings) against reference text.

An iterative application (multi-anchor mapping) of approximate string mapping to different anchor regions of a sequence read can prevent SNPs and repetitive regions of the reference sequence from seriously affecting the performance of the anchor-extension mapping method.

Figure 6:
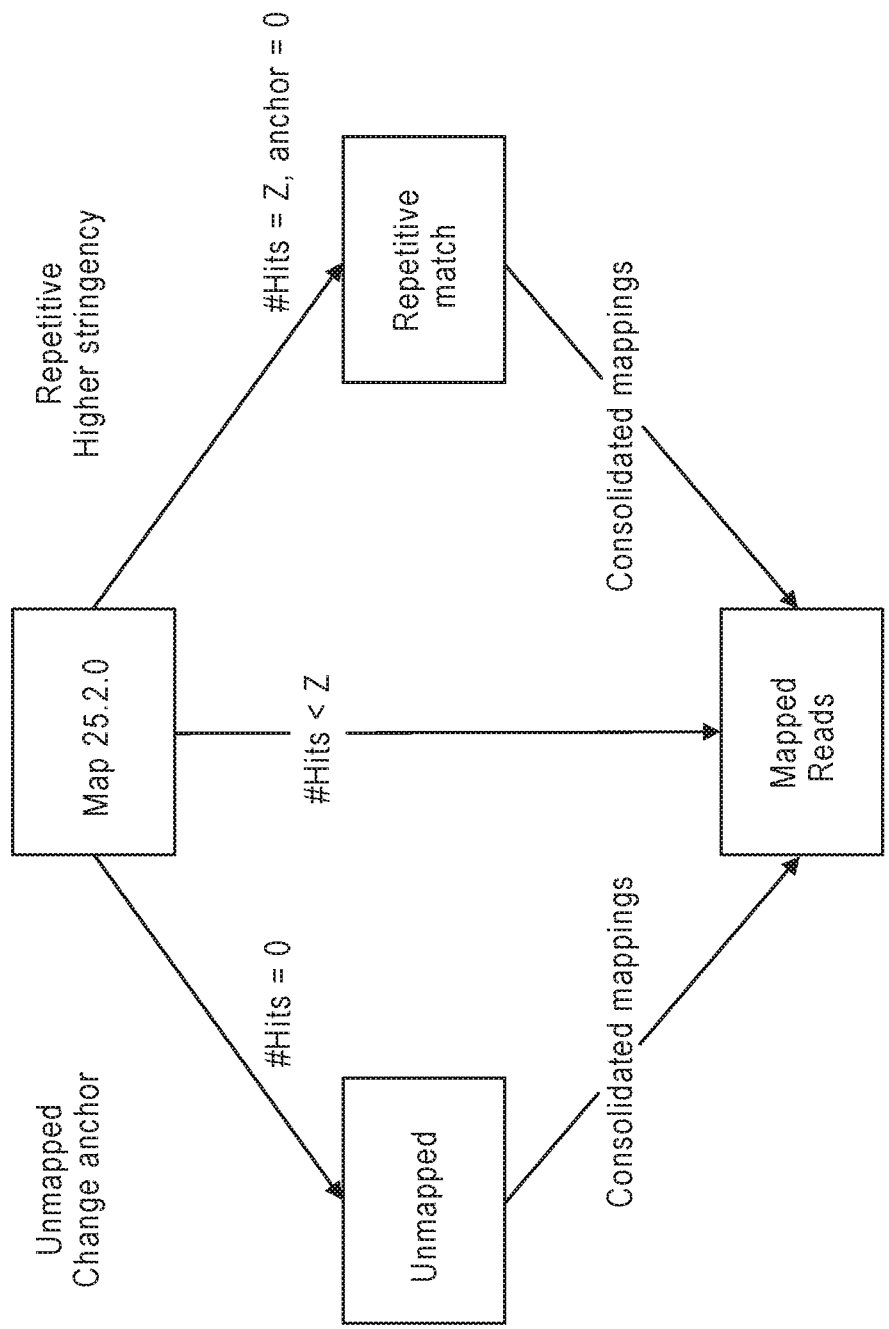
FIG. 6 is a flowchart illustrating a multi-anchor mapping method, in accordance with various embodiments.

FIG. 6 is a flowchart illustrating a multi-anchor extension mapping method, in accordance with various embodiments. As shown herein, approximate string mapping can be used to find hits to an initial anchor region (25 bases) of a sequence read with a set mismatch constraint (2 mismatches). Depending on how many hits are found for each read, the method can proceed in one of three workflows: finished, unmapped, or repetitive.

In various embodiments, if the number of hits found is between 1 and a threshold number Z, no further processing is done and the hits for that read are reported. In various embodiments, the threshold number Z is user defined. In various embodiments, the threshold number Z is automatically determined by the algorithm/script/program implementing the anchor-extension mapping method to maximize the accuracy of the read alignment.

Figure 8:
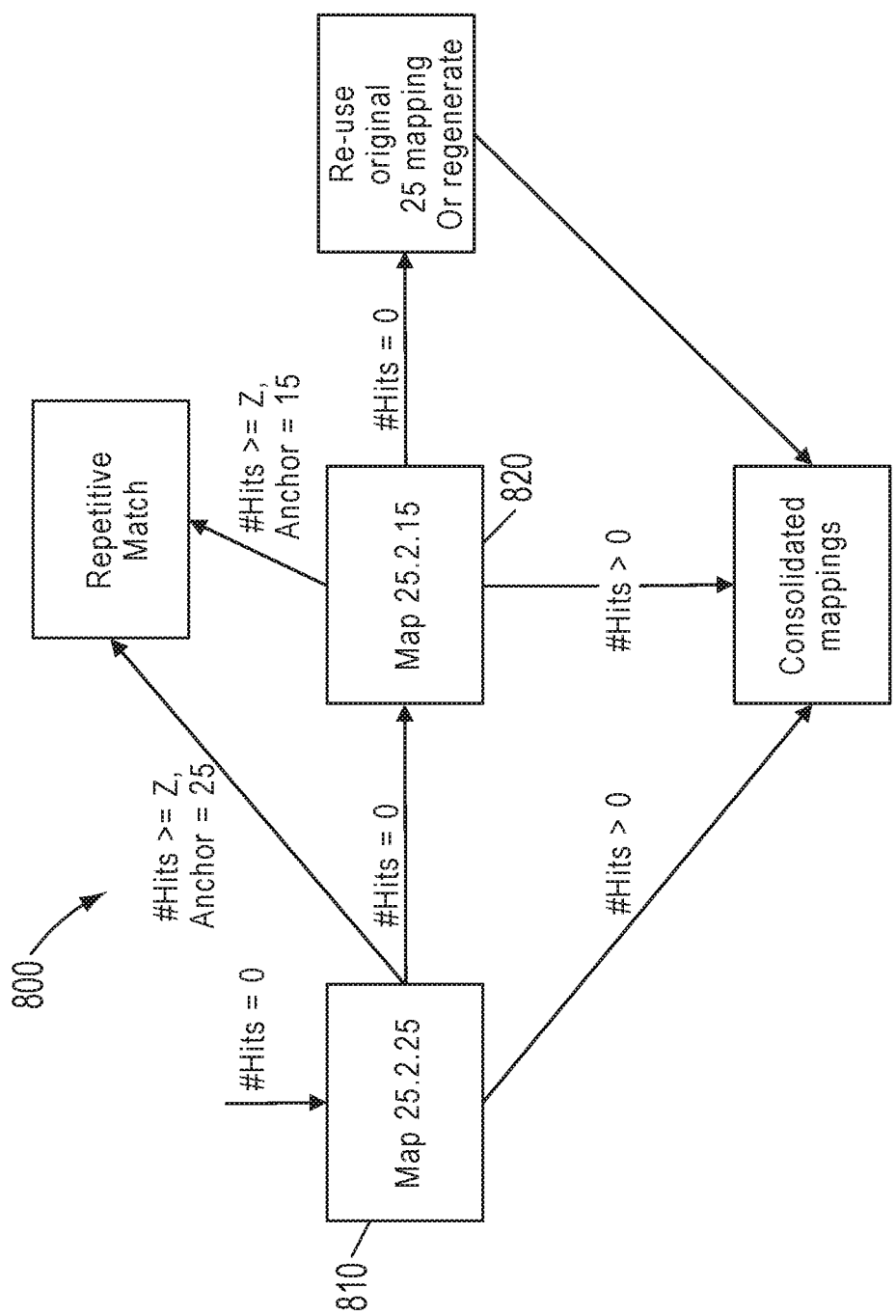
FIG. 8 is a flowchart illustrating a multi-anchor mapping method for aligning nucleic acid sequence reads that did not map to a reference sequence after an initial round of mapping, in accordance with various embodiments.

In various embodiments, if no hits are found, the method can proceed along the "unmapped" workflow where a different anchor region of the sequence read (with the same length as the initial anchor region) can be selected and mapped to the reference sequence. Approximate string mapping can then be used again to find hits to the different anchor region of the sequence read. As depicted in FIG. 8, this process can continue until a hit is found or all portions of the read have been used as an anchor region. For example, a first approximate string mapping can use the first 25 bases of a read as the anchor region and set a mismatch constraint of 2. For reads that do not have a hit, the next 25 bases or bases 15-39 of the read can be selected as the anchor region and another round of approximate string mapping is performed. If the number of hits found for the read is between 1 and a threshold number Z, the iterations stop and the hits are reported for that read. If the number of hits exceeds the threshold number Z, the methods proceeds to the "repetitive match" workflow.

Figure 7:
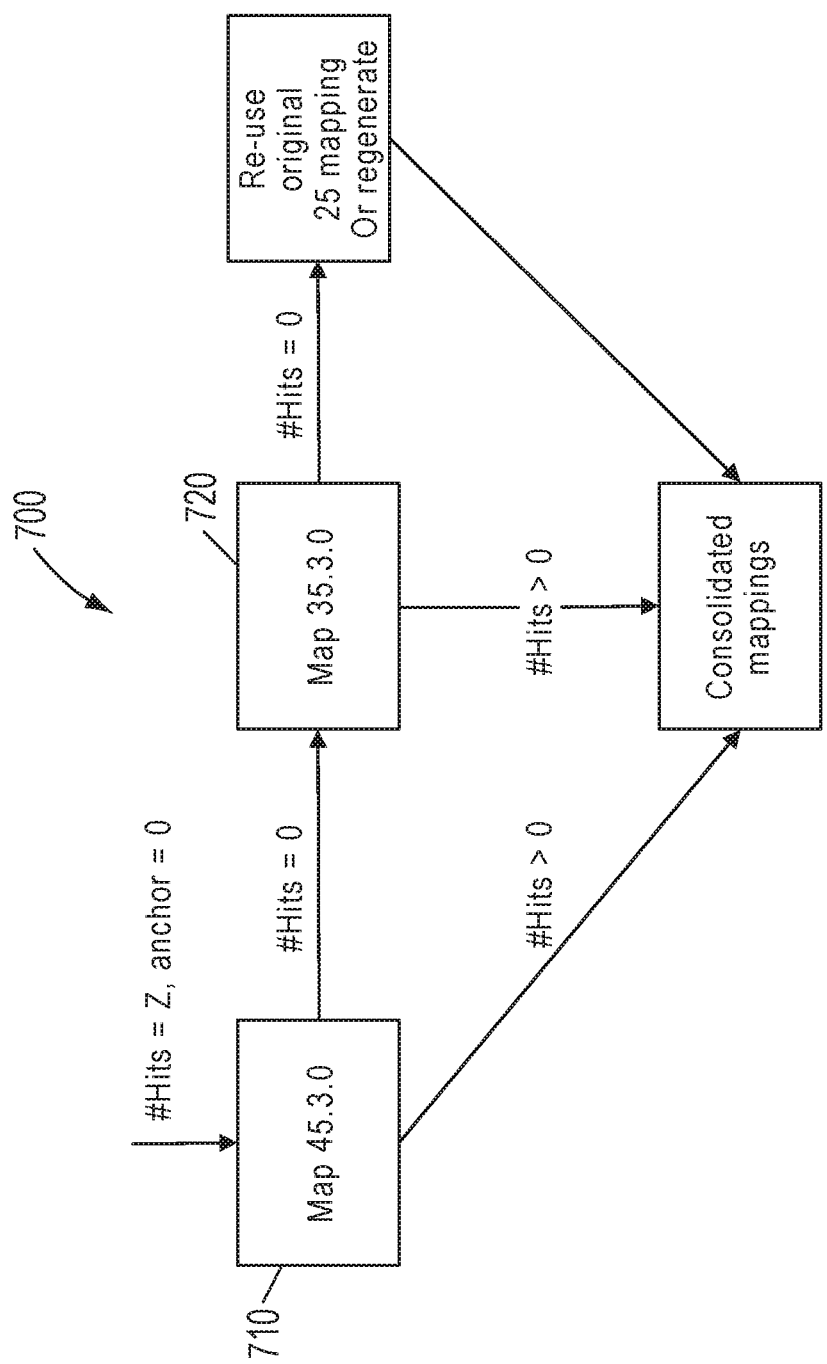
FIG. 7 is a flowchart illustrating a multi-anchor mapping method for aligning nucleic acid sequence reads that have repetitively mapped to a reference sequence after an initial round of mapping, in accordance with various embodiments.

In various embodiments, when the number of hits found for a read exceeds a certain threshold number Z, the method can proceed along the "repetitive match" workflow where the length of the anchor region is increased. Approximate string mapping is then again used to find hits to the anchor region of increased length. As depicted in FIG. 7, this process can continue iteratively until the number of hits found is less than or equal to a certain threshold number or the length of the anchor region is increased to the length of the sequence read. Anchor regions of greater length are used because this tends to increase the selectivity of the matching. For example, a first approximate string mapping can use the first 25 bases of a read as the anchor region. For reads that produce hits greater than a certain threshold, Z, the anchor region can be increased to the first 45 bases and another round of approximate string mapping can be performed. If the number of hits decreases to between 1 and the threshold number Z, the iterations stop and the hits are reported for that read. If the number of hits decreases to zero, the anchor region length is decreased to a length (e.g., 35 bases, etc.) that is between the 45 bases of the previous iteration and the 25 bases of the original mapping operation.

In various embodiments, after the set H of all the potential hits (h) of a nucleic acid sequence read is determined, a posterior likelihood L(h) for each h in H is calculated based on the local score of h and the base error rate (e) of the sequencing (i.e., error rate associated with the sequencing of the sample nucleic acid sequence read). More formally, L(h) is the probability of observing the read (the chance the read is as is), assuming the alignment h is correct (i.e., the read is sequenced from the alignment position). Assuming a uniform independent error rate of e, if the length of alignment is a, and number of mismatch is b, L(h) is simply $e^b*(1-e)^{(a-b)}$. Letting M be the sum of L(h) for all h in H, the mapping QV (MQV) of each hit h can be calculated as L(h)/M. For example, if a read has two hits of the same score, L(h1)=L(h2), M=L(h1)+L(h2) the MQV of each hit is 50%. In various embodiments, the read alignment with the highest MQV is designated as the primary alignment for the read.

In various embodiments, the anchor-extension mapping method runs can be controlled using three parameters. These three parameters can be denoted by three integers separated by dot. For example, the parameters of an anchor-extension mapping run can be denoted as 25.2.0, and the different parameters of another run can be denoted as 35.3.5. For the 25.2.0 run, 25 can represent an anchor region length of 25 bases, 2 can represent the number of mismatches allowed in the anchor region, and 0 can represent the starting position of the anchor region in the read sequence. Therefore, for the 25.2.0 run, the anchor region spans bases 0-24 of the read sequence. For the 35.3.5 run, 35 represents an anchor region length of 35 bases, 3 represents the number of mismatches allowed in the anchor region, and 5 represents the starting position of the anchor region in the read sequence. Therefore, for the 35.3.5 run the anchor region spans bases 5-39 of the read sequence.

In various embodiments, the anchor-extension mapping method runs can be controlled using four parameters. These parameters can include the three parameters described above and a parameter, Z, that is, the hit threshold number, which is also as described above. It should be appreciated, however, that the anchor-extension mapping method can be controlled using more or less parameters depending on the requirements of the particular application.

In various embodiments, all parameters of each anchor-extension mapping method run can be adjusted by a user during any iteration. A user can also select a customized iterative strategy.

It should be understood, however, that the multi-anchor extension mapping method depicted in FIGS. 6-8 can also be applied to map biological sequences other than nucleic acid sequences or even non-biological sequences. For example, the multi-anchor extension mapping method can be applied to map a sample protein sequence (basically a sequence comprised of amino acids) against a reference protein sequence in proteomics research. Alternatively, the multi-anchor extension mapping method can also be applied to map natural language text (text strings) against reference text.

In various embodiments, the anchor-extension mapping methods described above and depicted in FIGS. 3-8 can be implemented using one or more computing device (e.g., workstation, mainframe computer, server, personal computer, mobile device, etc.).

Figure 4:
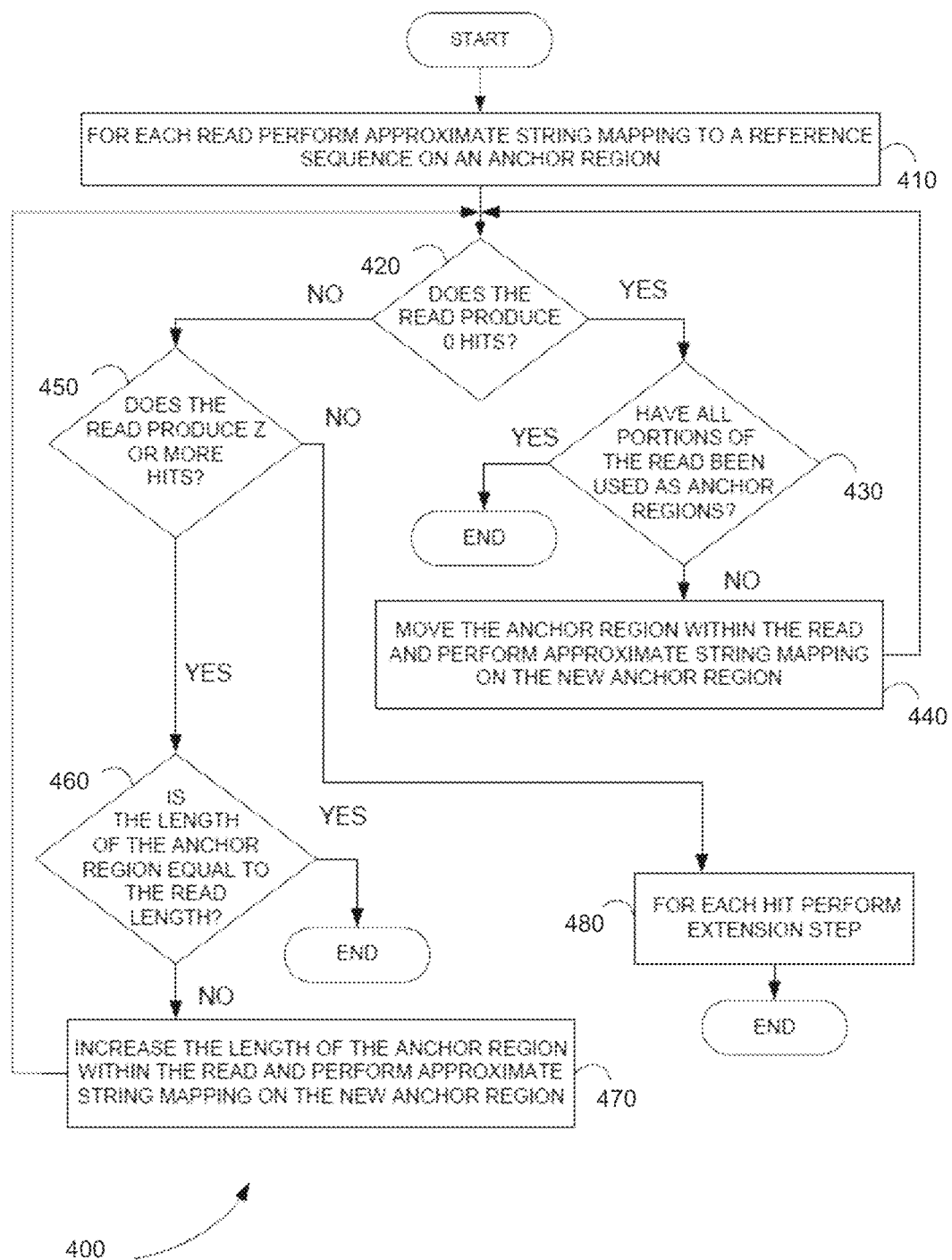
FIG. 4 is a flowchart showing an anchor-extension mapping method, in accordance with various embodiments.

FIG. 4 is a flowchart showing an anchor-extension mapping method 400, in accordance with various embodiments.

In step 410 of method 400, for each read sequence, approximate string mapping to a reference sequence is performed on an anchor region. In various embodiments, the anchor region is manually selected by a user. In various embodiments, the anchor region is automatically selected by the algorithm/script/program implementing the anchor-extension mapping method to maximize the accuracy of the read alignment.

In various embodiments the string mapping of the anchor region allows for a set number of mismatches (i.e., conforms to a set mismatch constraint). In various embodiments, the number of mismatches allowed is manually selected by a user. In various embodiments, the number of mismatches allowed is automatically selected by the algorithm/script/program implementing the anchor-extension mapping method to maximize the accuracy of the read alignment.

In step 420, it is determined if the read produces no hits. If there are no hits, approximate string mapping can be applied iteratively to different anchor regions of the sequence read starting at step 430. If there are hits, it is determined if the number of hits exceeds a certain threshold number Z, at step 450. In various embodiments, the threshold number Z is user defined. In various embodiments, the threshold number Z is automatically determined by the algorithm/script/program implementing the anchor-extension mapping method to maximize the accuracy of the read alignment.

In step 430, it is determined if all portions of the read have been used as anchor regions. If all portions of the read have been used, no hit can be found for the read and the anchor-extension stops for that read. In various embodiments, if no hit can be found for the read it can be regenerated. If all portions of the read have not been used, step 440 can be executed.

In step 440, the anchor region can be moved to a different location within the read, approximate string mapping can be performed on the new anchor region, and step 420 can be executed again.

In step 450, it is determined if the number of hits exceeds a certain threshold, Z. If the number of hits does not exceed the threshold, step 480 is executed. If the number of hits meets or exceeds the threshold, approximate string mapping can be applied iteratively to anchor regions of different length starting at step 460.

In step 460, it is determined if the length of the anchor region is equal to the read length. If the length of the anchor region is equal to the read length, too many hits were found for the read and method 400 stops mapping for that read. In various embodiments, the read can be regenerated. If the length of the anchor region is not equal to the read length, step 470 is executed.

In step 470, the length of the anchor region can be increased within the read and approximate string mapping can be performed on the new anchor region and step 420 is again executed.

In step 480, the extension step is performed for each hit.

In various embodiments, the method 400 can be performed using color space nucleic acid sequence data. In various embodiments, the method 400 can be performed using base space nucleic acid sequence data. It should be understood, however, that the method 400 disclosed herein can be performed using any schema or format of nucleic acid sequence information as long as the schema or format can convey the base identity and position.

In various embodiments, after the set H of all the potential hits (h) of a nucleic acid sequence read is determined, a posterior likelihood L(h) for each h in H is calculated based on the local score of h and the base error rate (e) of the sequencing (i.e., error rate associated with the sequencing of the sample nucleic acid sequence read). More formally, L(h) is the probability of observing the read (the chance the read is as is), assuming the alignment h is correct (i.e., the read is sequenced from the alignment position). Assuming a uniform independent error rate of e, if the length of alignment is a, and number of mismatch is b, L(h) is simply e^b*(1−e)^(a−b). Letting M be the sum of L(h) for all h in H, the mapping QV (MQV) of each hit h can be calculated as L(h)/M. For example, if a read has two hits of the same score, L(h1)=L(h2), M=L(h1)+L(h2) the MQV of each hit is 50%. In various embodiments, the read alignment with the highest MQV is designated as the primary alignment for the read.

It should be understood, however, that the anchor-extension mapping method 400 depicted in FIG. 4 can also be applied to map biological sequences other than nucleic acid sequences or even non-biological sequences. For example, the multi-anchor extension mapping method can be applied to map a sample protein sequence (basically a sequence comprised of amino acids) against a reference protein sequence in proteomics research. Alternatively, the multi-anchor extension mapping method can also be applied to map natural language text (text strings) against reference text.

Figure 5:
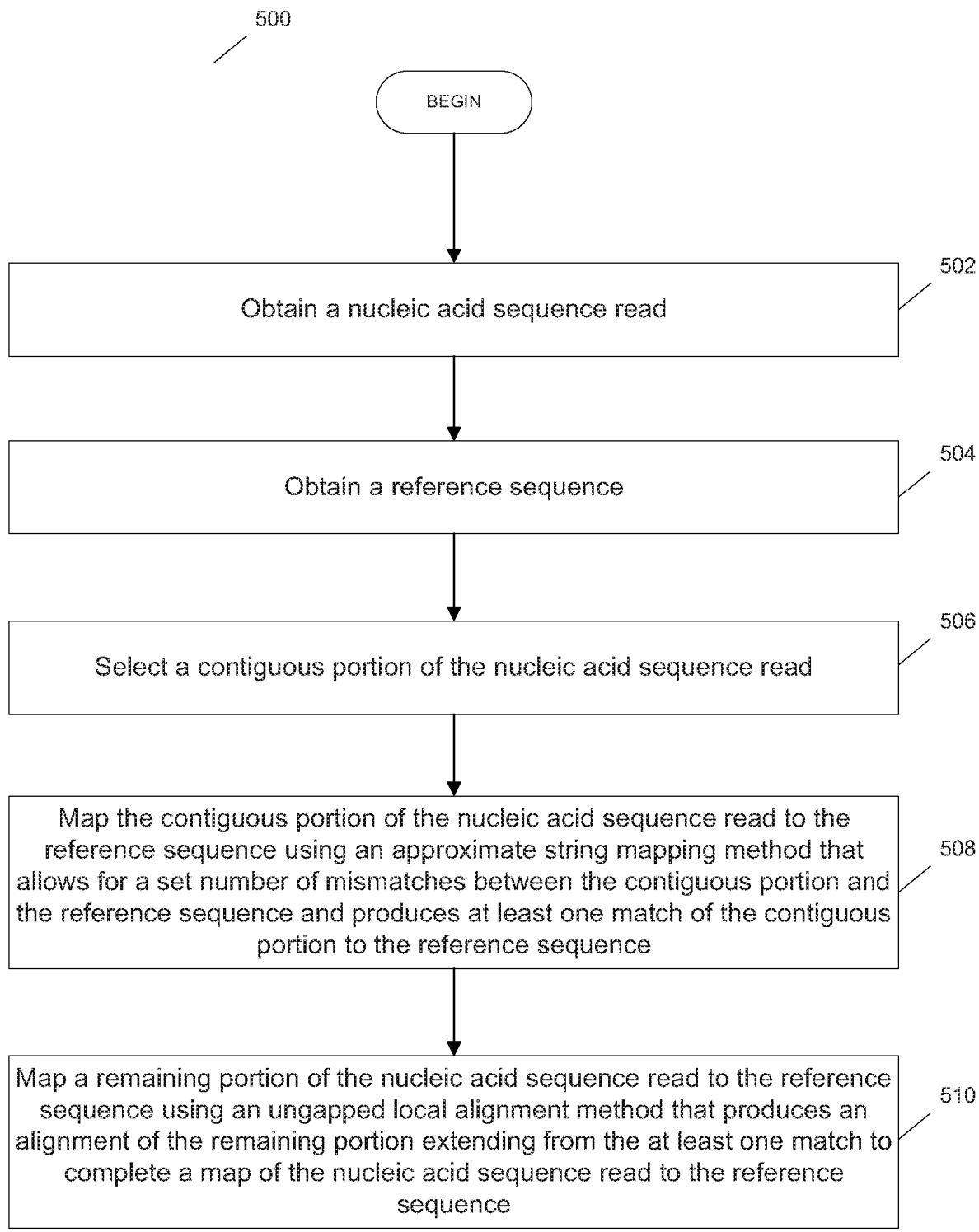
FIG. 5 is an exemplary flowchart showing a method for mapping a nucleic acid sequence read to a reference sequence, in accordance with various embodiments.

FIG. 5 is an exemplary flowchart showing a method 500 for anchor-extension mapping a read of a nucleic acid sequence to a reference sequence, in accordance with various embodiments.

In step 502, the nucleic acid sequence read is obtained. In various embodiments, the nucleic acid sequence read can be obtained from a nucleic acid sequence read data storage device. The nucleic acid sequence data storage device can be any database storage device, system or implementation (e.g., data storage partition, etc.) that is configured to organize and store nucleic acid sequence read data such that the data can be searched and retrieved manually (i.e., by a database administrator/client operator) or automatically by way of a computer program/application/software script. In various embodiments, the nucleic acid sequence read can be obtained directly from a nucleic acid sequencer in substantially real-time via a data cable (e.g., serial cable, direct cable connection, etc.) or bus linkage or, alternatively, through a network connection (e.g., Internet, LAN, WAN, VPN, etc.).

In step 530, a reference sequence is obtained. In various embodiments, the reference sequence read can be obtained from a reference sequence (e.g, genome, exome, etc.) data storage device. The reference sequence data storage device can be any database storage device, system or implementation (e.g., data storage partition, etc.) that is configured to organize and store reference sequence data such that the data can be searched and retrieved manually (i.e., by a database administrator/client operator) or automatically by way of a computer program/application/software script.

In step 540, a contiguous portion of the nucleic acid sequence read is selected.

In step 550, the contiguous portion is mapped to the reference sequence using an approximate string mapping method that allows for a set number of mismatches between the contiguous portion and the reference sequence and produces at least one match of the contiguous portion to the reference sequence.

In step 560, a remaining portion of the read is mapped to the reference sequence using an ungapped local alignment method that produces an alignment of the remaining portion extending from the match to complete a map of the nucleic acid sequence read to the reference sequence.

In various embodiments, the method 500 can be performed using color space nucleic acid sequence data. In various embodiments, the method 500 can be performed using base space nucleic acid sequence data. It should be understood, however, that the method 500 disclosed herein can be performed using any schema or format of nucleic acid sequence information as long as the schema or format can convey the base identity and position.

In various embodiments, after the set H of all the potential hits (h) of a nucleic acid sequence read is determined, a posterior likelihood L(h) for each h in H is calculated based on the local score of h and the base error rate (e) of the sequencing (i.e., error rate associated with the sequencing of the sample nucleic acid sequence read). More formally, L(h) is the probability of observing the read (the chance the read is as is), assuming the alignment h is correct (i.e., the read is sequenced from the alignment position). Assuming a uniform independent error rate of e, if the length of alignment is a, and number of mismatch is b, L(h) is simply e^b*(1−e)^(a−b). Letting M be the sum of L(h) for all h in H, the mapping QV (MQV) of each hit h can be calculated as L(h)/M. For example, if a read has two hits of the same score, L(h1)=L(h2), M=L(h1)+L(h2) the MQV of each hit is 50%. In various embodiments, the read alignment with the highest MQV is designated as the primary alignment for the read.

It should be understood, however, that the anchor-extension mapping method 500 depicted in FIG. 5 can also be applied to map biological sequences other than nucleic acid sequences or even non-biological sequences. For example, the multi-anchor extension mapping method can be applied to map a sample protein sequence (basically a sequence comprised of amino acids) against a reference protein sequence in proteomics research. Alternatively, the multi-anchor extension mapping method can also be applied to map natural language text (text strings) against reference text.

Bridging Mapped Read Gaps for De Novo and Resequencing Assembly

As discussed above, de novo assembly of reads generated by NGS platforms can be inherently difficult due to reads being short, having errors and being sequenced non-uniformly across genome. These limitations can result in fragmented assemblies consisting of multiple contigs separated by read gaps.

Described herein is a genome assembly (i.e., ASiD) workflow that emphasizes the availability of mate-paired/paired-end reads (paired reads) to address challenges in de novo assembly of short reads.

Figure 9:
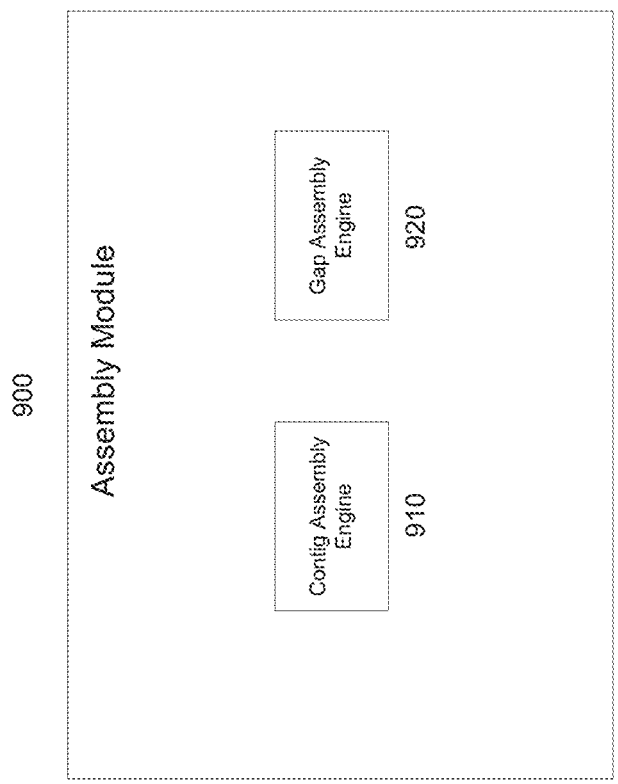
FIG. 9 is a schematic diagram of a de novo assembly module, in accordance with various embodiments.

FIG. 9 is a schematic diagram of an assembly module, in accordance with various embodiments. As disclosed herein, assembly module 900 includes a contig assembly engine 910 and a gap assembly engine 920 (i.e., ASiD module). The contig assembly engine 910 can be in communications with the gap assembly engine 920 and one or more sources of nucleic acid sequence read data. In various embodiments, the nucleic acid sequence read data can be obtained from a nucleic acid sequence data storage device. The nucleic acid sequence data storage device can be any database storage device, system or implementation (e.g., data storage partition, etc.) that is configured to organize and store nucleic acid sequence data such that the data can be searched and retrieved manually (i.e., by a database administrator/client operator) or automatically by way of a computer program/application/software script. In various embodiments, the nucleic acid sequence read data can be obtained directly from a nucleic acid sequencer in substantially real-time via a data cable (e.g., serial cable, direct cable connection, etc.) or bus linkage or, alternatively, through a network connection (e.g., Internet, LAN, WAN, VPN, etc.).

The contig assembly engine 910 is configured to take paired nucleic acid sequence reads and assemble them into larger sequences (i.e., contigs) with gap regions in between them that together can comprise a scaffold of a whole (or partial) genome or exome. Contig assembly engine 910 can be any conventional nucleic acid sequencing assembly algorithm or program including, but not limited to: VELVET, SOAPdenovo, ABySS, Forge, etc.

Gap assembly engine 920 can be configured to process the scaffold assembled by the contig assembly engine 910 to fill in the gap regions between the contigs using any "hanging" pairwise sequence 1010 of the assembled paired nucleic acid sequence reads (comprising the contigs). That is, each of the paired nucleic acid sequence reads is comprised of a pair of pairwise sequences separated by an intervening length. When these reads are assembled to form a contig only one of the pair of pairwise sequences is typically assembled leaving a hanging pairwise sequence that is either not assembled or assembled as part of another contig.

Figure 10A:
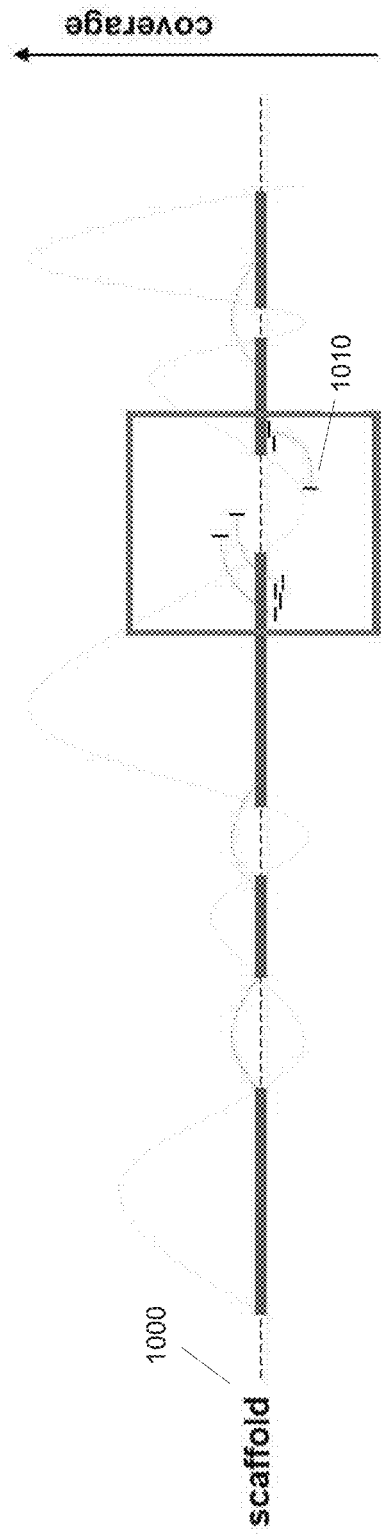
FIGS. 10A and 10B are diagrams showing how ASiD assembly technique can be applied to de novo assembly applications to fill in gap areas in a nucleic acid sequence scaffold assembled from mate-pair or paired-end nucleic acid sequences, in accordance with various embodiments.
Figure 10B:
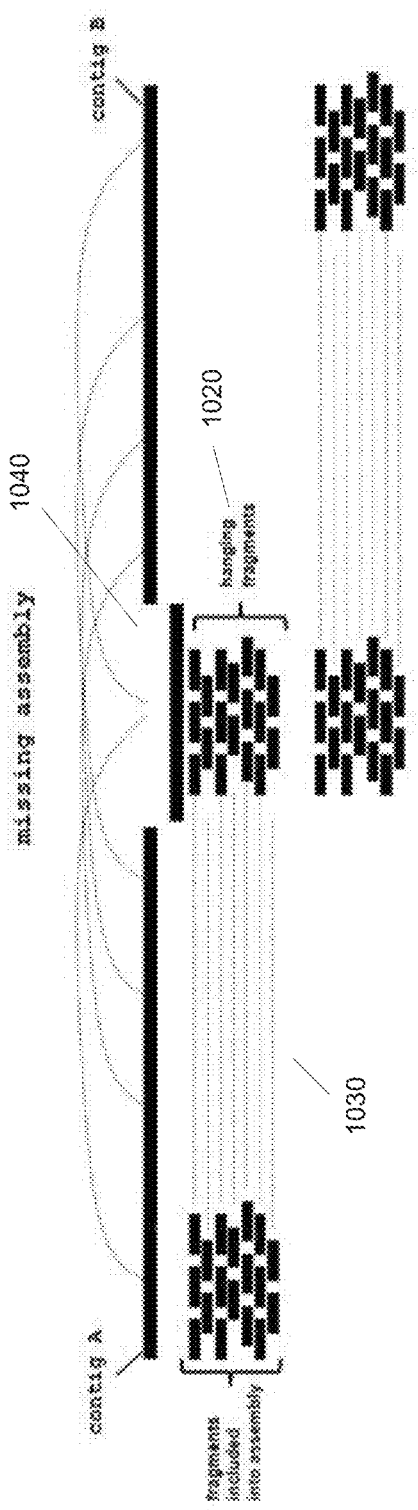

For example, as depicted in FIG. 10A, the scaffold 1000 assembled by the contig assembly engine 910 is comprised of a plurality of contigs that are separated by gap regions. The hanging pairwise sequences of the assembled reads (that form the contigs) can be assembled to fill in the gap regions of the scaffold 1000. This is clearly illustrated in FIG. 10B where the various hanging fragments 1020 of the assembled reads 1030 are shown overlapping one another in the gap region 1040.

It should be understood, however, that the various engines shown as being part of the assembly module 900 can be combined or collapsed into a single engine, depending on the requirements of the particular application or system architecture. Moreover, in various embodiments, the assembly module 900 can comprise additional engines or components as needed by the particular application or system architecture.

In various embodiments, the assembly module 900 can be configured to process the nucleic acid reads in color space. In various embodiments, the assembly module 900 can be configured to process the nucleic acid reads in base space. It should be understood, however, that the assembly module 900 disclosed herein can process or analyze nucleic acid sequence data in any schema or format as long as the schema or format can convey the base identity and position of the nucleic acid sequence.

Mapping Optimized tor Targeted Resequencing Applications

As discussed above, one of the defining attributes of NGS platforms is that they can produce 10-100's of millions of short reads in a single run. This allows the platforms to be used for high-throughput resequencing of nucleic acid samples to discover and genotype variants simultaneously. Resequencing experiments are fundamental in basic and clinical research as scientists look for causative mutations within populations. Targeted resequencing provides a mechanism to restrict sequencing analysis to specific regions of interest within the genome being studied. This comparative analysis of candidate genes or regions requires a high level of accuracy to identify low frequency SNPs and structural variants. Embodiments of optimized systems and methods for mapping a read of a nucleic acid sequence to a reference sequence in targeted resequencing type applications are described herein.

Figure 12:
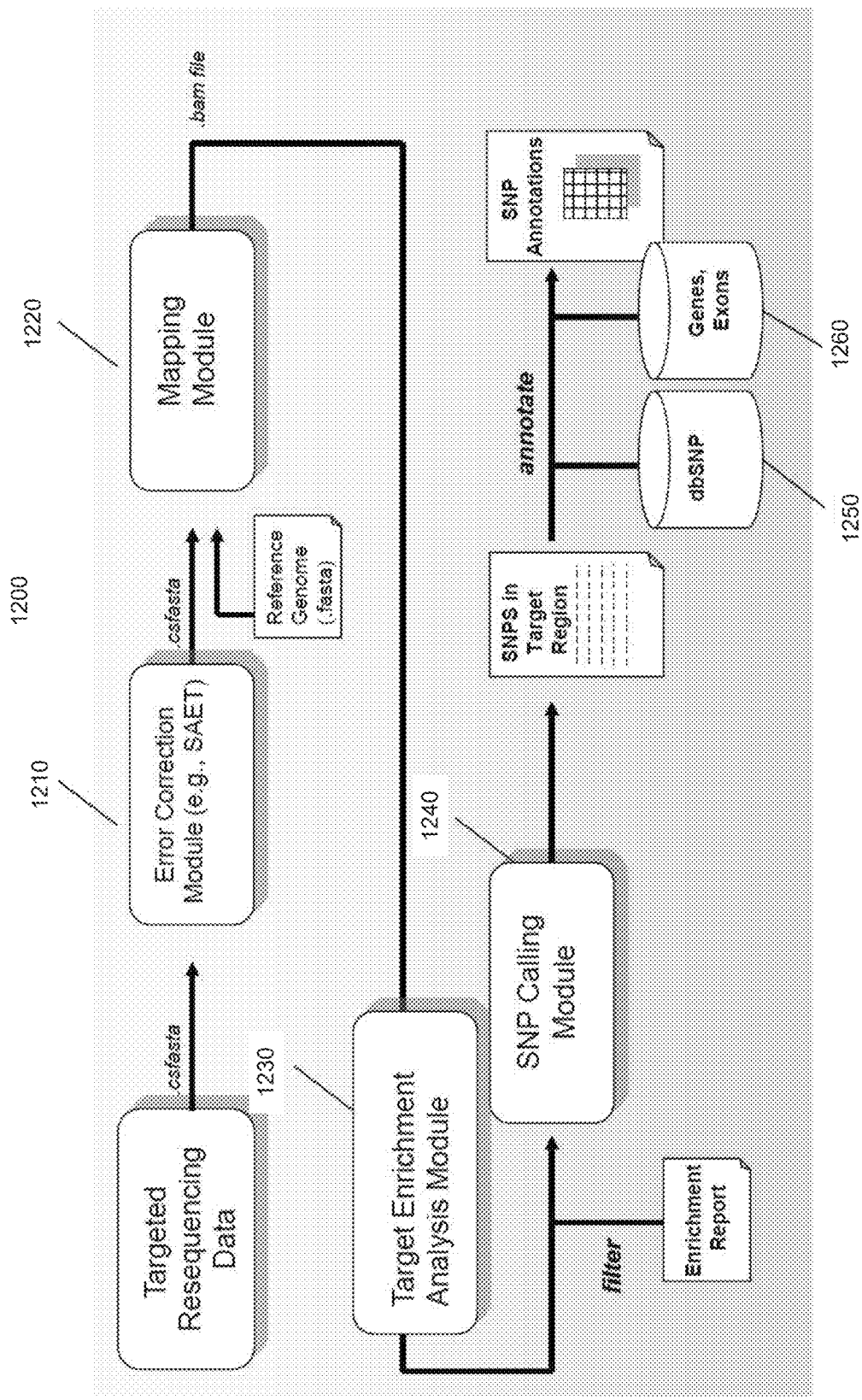
FIG. 12 is a schematic diagram of a system of distinct software modules that perform the optimized method for mapping nucleic acid sequence reads to a reference sequence for targeted resequencing applications, in accordance with various embodiments.

FIG. 12 is a schematic diagram of a system of distinct software modules performing an optimized method for mapping a read of a nucleic acid sequence to a reference sequence for targeted resequencing applications, in accordance with various embodiments.

System 1200 includes an optional error correction module 1210 (e.g., SAET, etc.), a mapping module 1220, a target enrichment analysis module 1230, a SNP detection module 1240, a SNP locator database 1250 and an exon locator database 1260. In various embodiments, the error correction module 1210 receives a read from a nucleic acid sequencer that interrogates a nucleic acid sample.

Error correction module 1210 (e.g., SAET, etc.) can be configured to improve the accuracy of reads by applying frequency spectrum data to the reads. In various embodiments, the error correction module 1210 can be optimized for targeted resequencing to maximize the accuracy of subsequent tertiary analyses (such as SNP accuracy in the presence of highly variable coverage) performed on the mapped reads.

Mapping module 1220 can be configured to perform a number of different steps. Mapping module 1220 can obtain a reference sequence and select a contiguous portion of the sequence read in accordance with a mapping algorithm or logic. In various embodiments, mapping module 1220 can map the contiguous portion to the reference sequence using an approximate string mapping method that produces at least one match of the contiguous portion to the reference sequence. The mapping module 1220 can map a remaining portion of the read to the reference sequence using an ungapped local alignment method that produces an alignment of the remaining portion extending from the match to complete a map of the read. Finally, the mapping module 1220 can generate an indexed binary format file (e.g., *.BAM file) that stores the mapped reads. It should be appreciated, however, that the mapping module 1220 can perform any or none of these steps depending on the requirements of the particular application.

Target enrichment module 1230 can be configured to identify the target enriched regions of the reference genome and/or filter the *.BAM file to include only reads that are on or close to the target enriched regions. In various embodiments, the target enrichment analysis module 1230 can also be configured to generate an enrichment report to summarize a variety of information relating to the mapped sequence reads, including but not limited to: counting the number/percent of sequence reads that have been mapped to the target enrichment regions, percentage of the targeted genome covered to different levels, percentage of each targeted enriched regions covered by a mapped sequence read, etc.

SNP calling module 1240 can be configured to make a SNP call. It should be understood, however, that the SNP calling module 1240 represents just one type of tertiary analysis module that can be operatively connected to the target enrichment module 1230. In practice, the SNP calling module 1240 can be substituted with many different types of tertiary analysis modules that can perform a variety of tertiary analysis on the filtered *.BAM file generated by the target enrichment module 1230. Examples of types of tertiary analysis include, but are not limited to: finding of inversions, finding insertions and deletions, finding of single nucleotide polymorphism (SNPs), counting of known exons, etc. In fact, the SNP module is optimized for targeted resequencing detection of SNPs by allowing SNP detection of reads with extremely high coverage (this is different than the way SNP calling is done in whole genome sequencing).

SNP database 1250 can be a data storage component configured to store data related to each SNP identified by the SNP calling module 1240.

Exon locator database 1260 can be a data storage component configured to store data related to exon locations on a genome.

As discussed previously, targeted resequencing is a workflow designed for the analysis of target enriched sequencing data. Given a set of coordinates representing a region of interest in a genome, a library can be enriched for reads within those regions prior to sequencing.

In general, the workflow for analysis of target enriched data is nearly identical to a standard mapping workflow discussed above. In fact, adequate results can be obtained using the standard mapping workflow as the targeted resequencing application consists of many of the same modules as the standard resequencing analysis. However, additional modules can be added for targeted resequencing analysis, and other modules can have specific parameters set that are optimized for analysis of targeted resequencing data. The error correction module 1210 can be enabled by default for enriched runs, as the smaller target size makes spectral error correction viable, even if it may not be practical for unenriched sequencing runs on a large reference sequence.

The target enrichment module 1230 module can be unique to the targeted resequencing application and addresses the uniformity and completeness of coverage within the target region, calculates the degree of enrichment, and produces a filtered *.BAM file for later variant calling by a tertiary analysis module such as the SNP calling module 1240.

It should be understood, however, that the various modules and engines shown as being part of the system 1200 can be combined or collapsed into a single engine, depending on the requirements of the particular application or system architecture. Moreover, in various embodiments, the system 1200 can comprise additional engines or components as needed by the particular application or system architecture.

In various embodiments, the module sand engines that comprise system 1200 can be configured to process the nucleic acid reads in color space. In various embodiments, the modules and engines that comprise system 1200 can be configured to process the nucleic acid reads in base space. It should be understood, however, the modules and engines that comprise system 1200 can process or analyze nucleic acid sequence data in any schema or format as long as the schema or format can convey the base identity and position of the nucleic acid sequence.

Figure 13:
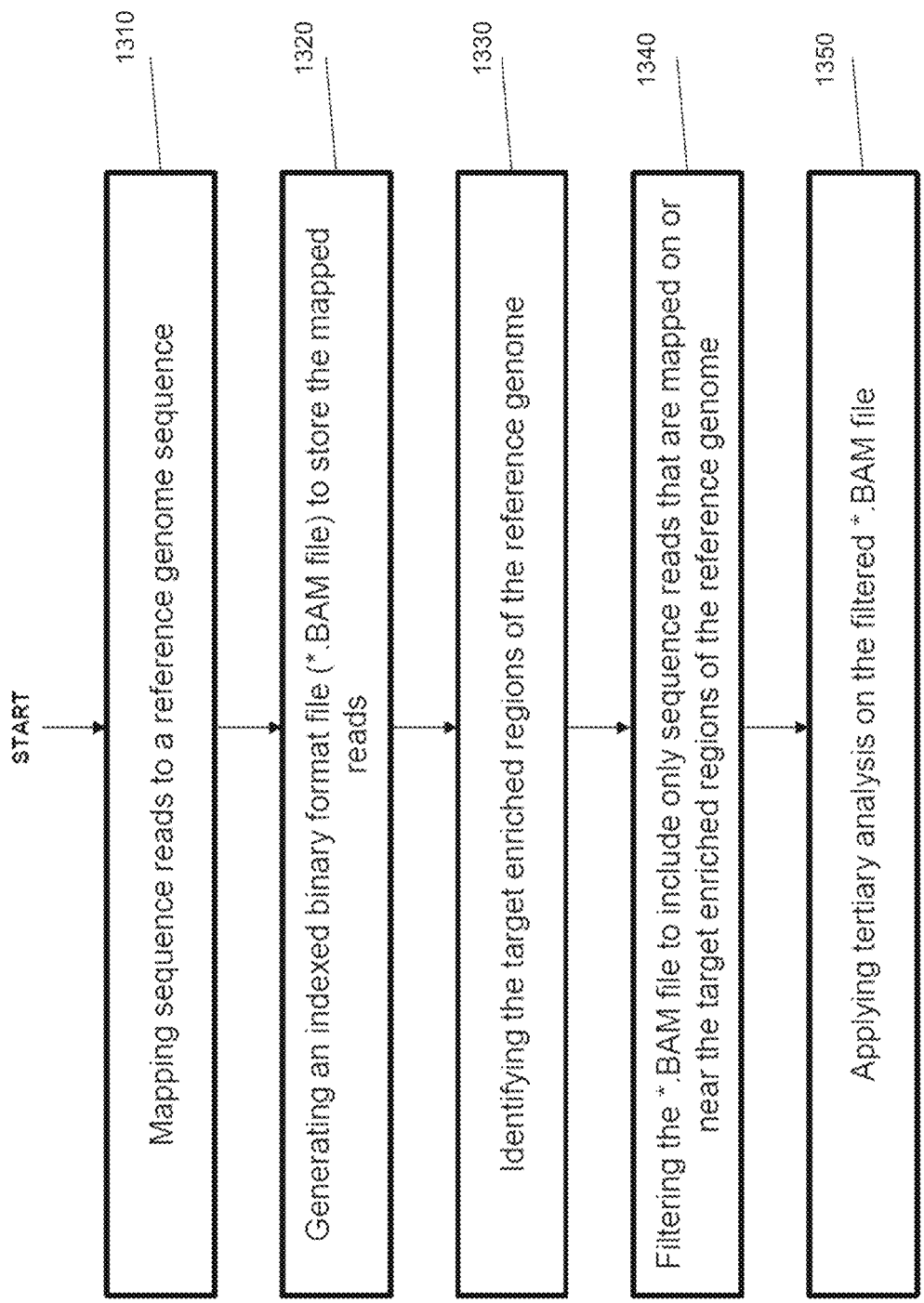
FIG. 13 is an exemplary flowchart showing an optimized method for mapping nucleic acid sequence reads to a reference sequence for targeted resequencing applications, in accordance with various embodiments.

FIG. 13 is an exemplary flowchart showing a method for mapping a read of a nucleic acid sequence to a reference sequence that is optimized for targeted resequencing applications, in accordance with various embodiments.

In step 1310, sequence reads produced from a nucleic acid sample using a nucleic acid sequencer are mapped to a reference genome sequence. In various embodiments, the reference genome sequence represents a whole genome of the subject being sequenced. In various embodiments, the reference genome sequence represents a portion of the whole genome of the subject being sequenced.

In various embodiments, the sequence reads are first processed by an error correction algorithm (e.g., SOLID Accuracy Enhancement Tool (SAET), etc.) prior to being mapped against the reference genome.

In step 1320, an indexed binary format file (*.BAM file) storing the mapped reads is generated.

In step 1330, the target enriched regions of the reference genome are identified.

In various embodiments, a report can also be generated to summarize a variety of information relating to the mapped sequence reads, including but not limited to: counting the number/percent of sequence reads that have been mapped to the target enrichment regions, percentage of the targeted genome covered to different levels, percentage of each targeted enriched regions covered by a mapped sequence read, etc.

In step 1340, the *.BAM file can be optionally filtered to include only sequence reads that are mapped on or near the target enriched regions of the reference genome.

In step 1350, tertiary analysis is applied on the filtered *.BAM file. That is, the mapped genome data contained in the filtered *.BAM file is further analyzed to generate biological interpretation.

Examples of types of tertiary analysis include, but are not limited to: finding of inversions, finding insertions and deletions, finding of single nucleotide polymorphism (SNPs), counting of known exons, etc.

In various embodiments, the method 1300 can be performed using color space nucleic acid sequence data. In various embodiments, the method 1300 can be performed using base space nucleic acid sequence data. It should be understood, however, that the method 1300 disclosed herein can be performed using any schema or format of nucleic acid sequence information as long as the schema or format can convey the base identity and position.

Duplicate Mapped Read Marking

One problem that frequently arises in targeted resequencing type applications is that duplicate sequence segments can often be presented to a sequencer to be sequenced and read. When the segment reads are mapped, the duplicate alignments can be marked as duplicate by the mapping algorithm. That is, a mark duplicates subroutine within the mapping algorithm examines all of the records in a *.BAM file and decides which reads (associated with a bead) are duplicates of other reads (associated with other beads). Generally speaking, there are two types of duplicates: optical duplicates, which are caused by defects in the primary analysis software, and PCR duplicates, which are caused by unwanted PCR reactions that occur after library preparation is complete. However from a computational point of view, optical duplicates and PCR duplicates are indistinguishable, so they are represented in the *.BAM file by enabling flag.

One way to determine if two sequence reads are duplicates or not is to compare the base sequences for each of the tags; two duplicate reads should have duplicate base sequences. However, due to sequencing errors, it may be the case that two duplicate reads are sequenced such that a sequencing error for one read will cause its base sequence to differ significantly from the other read. Therefore, rather than compare base sequences to determine if two reads are duplicates, their alignments can be compared instead. If two reads are duplicates, then the entire set of alignments for both reads should be the same.

The challenge comes in identifying these duplicate reads in input files (containing raw segment read data) that are very large (several hundred GB is typical) as they can often overwhelm machine memory which can significantly slow down processing speed. The root of this problem lies in how conventional mapping algorithms work to identify read duplicates. That is, conventional mapping algorithms typically need to analyze the whole input file and compare all potential alignments for each sequence to determine whether to mark each pair of reads a duplicate, which can be computationally prohibitive.

Embodiments of systems and methods for marking duplicate mapped reads of a nucleic acid sequence are described herein.

In one aspect, these systems and methods overcome the challenges inherent in conventional duplicate marking by only considering the primary alignments for the reads when making a duplicate call.

In various embodiments, among a set of N reads, each of which are mutual duplicates, all reads are marked as duplicates except one of them, which will be considered the read from which the other N-1 duplicates were generated from. In these cases, the non-duplicate read is the one whose primary alignment has the highest mapping (pairing) score. In cases where there are ties between mapping (pairing) qualities, the non-duplicate read is the one with the largest sum of base qualities. In cases where there are ties between sums of base qualities, the non-duplicate read is selected randomly; the randomness is deterministic to ensure that results are reproducible between runs.

Figure 14:
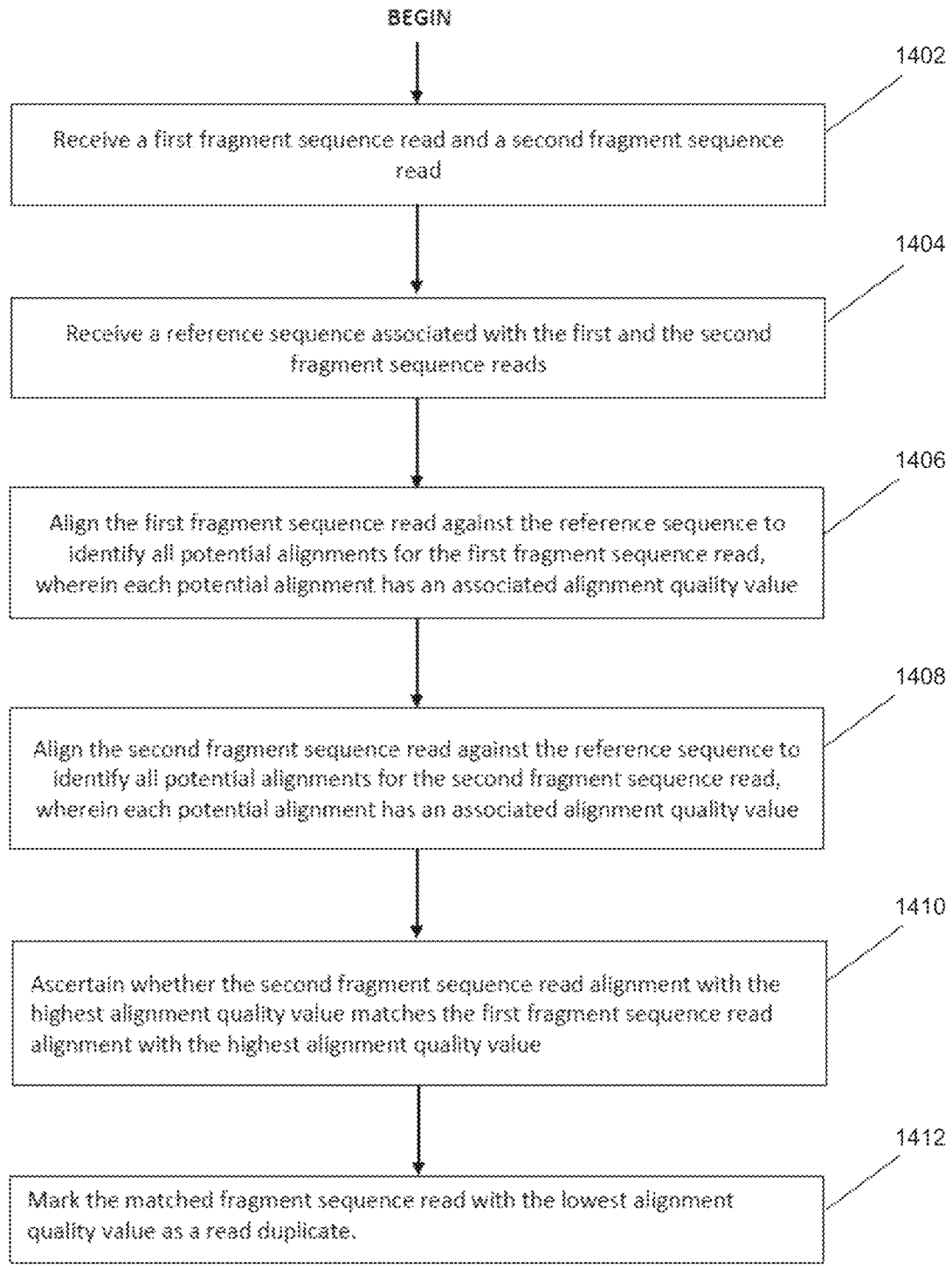
FIG. 14 is a detailed illustration of an example process for marking duplicate sequence reads, in accordance with various embodiments.

FIG. 14 is a detailed illustration of an example process for marking duplicate sequence reads, in accordance with various embodiments. As depicted herein, in step 1402, a first fragment sequence read and a second fragment sequence read are received. In various embodiments, the fragments are single continuous fragment reads. In various embodiments, the fragments are mate-pair/paired-end fragments. In step 1404, a reference sequence associated with the first and the second fragment sequence reads is received. In step 1406, the first fragment sequence read is aligned against the reference sequence to identify all potential alignments for the first fragment sequence read, wherein each potential alignment has an associated alignment quality value. In step 1408, the second fragment sequence read is aligned against the reference sequence to identify all potential alignments for the second fragment sequence read, wherein each potential alignment has an associated alignment quality value. In various embodiments the alignment quality value can be calculated by using an alignment scoring function where score (i,j)=M+mx, where M is the number of matches in the extended alignment, x is the number of mismatches in the alignment, and m is a negative penalty for each mismatch. In various embodiments, the negative penalty, m, for each mismatch is user defined. In various embodiments, the negative penalty, m, for each mismatch is automatically determined by the algorithm/script/program implementing the anchor-extension mapping method to maximize the accuracy of the read alignment.

In step 1410, a determination is made as to whether the second fragment sequence read alignment with the highest alignment score (i.e., the "primary alignment") matches the first fragment sequence read alignment with the highest alignment quality value (i.e., the "primary alignment"). In step 1412, the matched fragment sequence read with the lower alignment quality value is marked as a read duplicate. In situations where there is a tie between alignment (pairing) score from the matched fragment sequence reads, the fragment sequence read with the largest sum of base calling quality values will be designated as the non-duplicate read. In situations where there is a tie between the sums of the base calling quality values from the matched fragment sequence reads, the non-duplicate fragment read is randomly designated in a deterministic fashion to ensure that the results are reproducible between runs.

Figure 15:
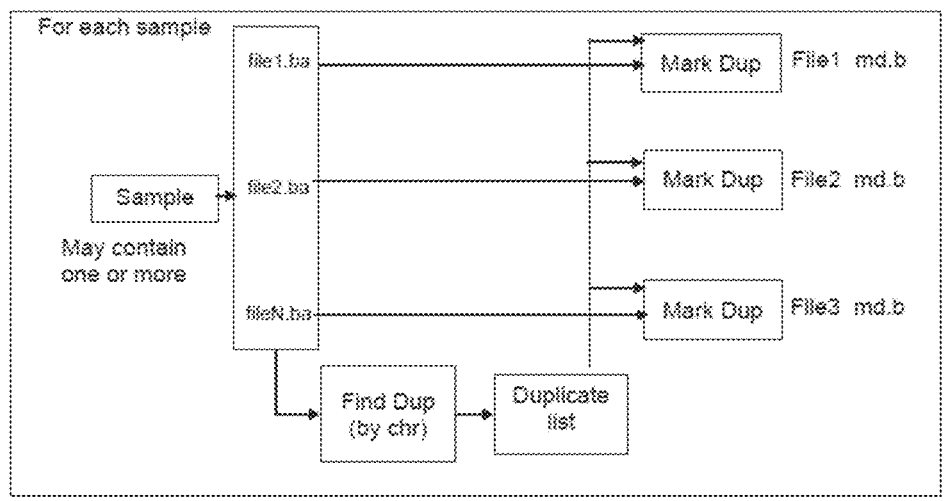
FIG. 15 is an exemplary flowchart showing the mark duplicates method being performed in two passes, in accordance with various embodiments.

In various embodiments, although only the primary alignments are examined in making duplicate calls, every alignment for a read is marked as a duplicate once the read is determined to be a duplicate. Thus, as depicted in FIG. 15, the mark duplicates subroutine performs its work in two passes: the first pass through the *.BAM file determines which reads are duplicates, and the second pass actually marks them.

In various embodiments, the method 1400 can be performed using color space nucleic acid sequence data. In various embodiments, the method 1400 can be performed using base space nucleic acid sequence data. It should be understood, however, that the method 1400 disclosed herein can be performed using any schema or format of nucleic acid sequence information as long as the schema or format can convey the base identity and position.

In another aspect, these systems and methods overcome the challenges inherent in conventional duplicate marking techniques by converting and storing compact representations of the mapped read sequence information (from the input file) into machine memory prior to the mark duplicate identification step. This allows the mark duplication step to be done on the fly by streaming the file, analyzing the sequence reads one by one (each time using the information stored in the main memory to make the decision of whether a read is a duplicate) and outputting the duplicate reads with the duplicate mark. In this manner, very large input files to be processed quickly and efficiently.

In various embodiments, the compact representation of the mapped read sequence information can be stored in a hash table in a format that allows for only a portion of the compact representation to be analyzed during the mark duplication step before a read sequence duplicate call is made. For example, where the compact representation of a mapped read sequence contains 43 bits of data, the hash table can designate a portion (for example, the first 28 bits) of that compact representation for an initial analysis during the mark duplication step. When there is a match between the first 28 bits of the compact representation of any two read sequences, a follow-on analysis is done for the remaining 15 bits of each sequence to make a final determination as to whether one of the sequences is a duplicate.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system for nucleic acid sequence assembly, comprising:
   a first data storage configured to store nucleic acid sequencing data;
   a second data storage configured to store reference genome data; and
   a computing device in communication with the first data storage and the second data storage, wherein the computing device is configured to:
      obtain a nucleic acid sequence read from the first data storage,
      obtain a reference genome from the second data storage,
      iteratively select anchor sequences comprising differing lengths of a contiguous portion of the nucleic acid sequence read, wherein each anchor sequence begins at a same location on the nucleic acid sequence read,
      map the anchor sequence to the reference genome using an approximate string mapping method that allows for a set number of mismatches with the reference genome and produces at least one match with the reference genome, wherein the iterative selection and mapping of the anchor sequence is performed until a number of matches of the anchor sequence to the reference genome is less than a threshold number,
      map a remaining portion of the nucleic acid sequence read to the reference genome using an ungapped local alignment method that produces an alignment of the remaining portion extending from the at least one match to map the nucleic acid sequence read to the reference genome,
      generate an indexed binary file that stores the mapping of the anchor sequence and the remaining portion to the reference genome,
      filter the indexed binary file to generate a filtered indexed binary file, the filtered indexed binary file comprising nucleic acid sequence reads that are mapped to target enriched regions in the reference genome, and
      perform a resequencing analysis on the filtered indexed binary file to assemble a nucleotide sequence based on the nucleotide sequence read.

2. The system of claim 1, wherein the computing device is further configured to automatically select the contiguous portion of the nucleic acid sequence read.

3. The system of claim 1, wherein the alignment of the remaining portion extends from the at least one match in either direction.

4. The system of claim 1, wherein the ungapped local alignment method uses a scoring function to select the alignment of the remaining portion.

5. The system of claim 4, wherein the scoring function is a sum of a number of matches in the alignment and a product of a number of mismatches in the alignment and a negative penalty for each mismatch.

6. The system of claim 1, wherein the set number of mismatches is pre-selected.

7. The system of claim 1, wherein the first data storage and the second data storage are hosted on a single data storage device.

8. The system of claim 1, wherein at least one of the first data storage and the second data storage are hosted on the computing device.

9. The system of claim 8, wherein both the first data storage and the second data storage are hosted on the computing device.

10. The system of claim 8, wherein the first data storage is hosted by a nucleic acid sequencer.

11. A computer implemented method for nucleic acid sequence assembly, the method comprising:
obtaining a nucleic acid sequence read;
obtaining a reference genome;
iteratively selecting anchor sequences comprising differing lengths of a contiguous portion of the nucleic acid sequence read, wherein each anchor sequence begins at a same location on the nucleic acid sequence read;
mapping, using a processor, the anchor sequence to the reference genome using an approximate string mapping method that allows for a set number of mismatches with the reference genome and produces at least one match with the reference genome, wherein the iteratively selecting and mapping of the anchor sequence is performed until a number of matches of the anchor sequence to the reference genome is less than a threshold number;
mapping, using the processor, a remaining portion of the nucleic acid sequence read to the reference genome using an ungapped local alignment method that produces an alignment of the remaining portion extending from the at least one match to map the nucleic acid sequence read to the reference genome;
generating an indexed binary file that stores the mapping of the anchor sequence and remaining portion to the reference genome;
filtering the indexed binary file to generate a filtered indexed binary file, the filtered indexed binary file comprising nucleic acid sequence reads that are mapped to target enriched regions in the reference genome; and
performing a resequencing analysis on the filtered indexed binary file to assemble a nucleotide sequence based on the nucleotide sequence read.

12. The method of claim 11, wherein the alignment of the remaining portion extends from the at least one match in either direction.

13. The method of claim 11, wherein the ungapped local alignment method uses a scoring function to select the alignment.

14. The method of claim 13, wherein the scoring function is a sum of a number of matches in the alignment and a product of a number of mismatches in the alignment and a negative penalty for each mismatch.

15. A non-transitory computer-readable storage medium comprising:
a program with instructions to be executed by a processor so as to perform a method for nucleic acid sequence assembly, the method comprising:
receiving a nucleic acid sequence read;
obtaining a reference genome;
iteratively selecting anchor sequences comprising differing lengths of a contiguous portion of the nucleic acid sequence read, wherein each anchor sequence begins at a same location on the nucleic acid sequence read;
mapping the anchor sequence to the reference genome using an approximate string mapping method that allows for a set number of mismatches with the reference genome and produces at least one match with the reference genome, wherein the iteratively selecting and mapping of the anchor sequence is performed until a number of matches of the anchor sequence to the reference genome is less than a threshold number;
mapping a remaining portion of the read to the reference genome using an ungapped local alignment method that produces an alignment of the remaining portion extending from the at least one match to map the nucleic acid sequence read to the reference genome;
generating an indexed binary file that stores the mapping of the anchor sequence and remaining portion to the reference genome;
filtering the indexed binary file to generate a filtered indexed binary file, the filtered indexed binary file comprising nucleic acid sequence reads that are mapped to target enriched regions in the reference genome; and
performing a resequencing analysis on the filtered indexed binary file to assemble a nucleotide sequence based on the nucleotide sequence read.

16. The non-transitory computer-readable storage medium of claim 15, wherein the alignment of the remaining portion extends from the at least one match in either direction.

17. The non-transitory computer-readable storage medium of claim 15, wherein the ungapped local alignment method uses a scoring function to select the alignment.

18. The non-transitory computer-readable storage medium of claim 17, wherein the scoring function is a sum of a number of matches in the alignment and a product of a number of mismatches in the alignment and a negative penalty for each mismatch.

19. The system of claim 1, wherein the computing device is further configured to:
iterate the map steps such that a plurality of alignments for the obtained nucleic acid sequence read are determined;
calculate a quality value for each of the plurality of alignments based on a base error rate, a length for the alignment, and a number of mismatches for the alignment; and
select the alignment with a greatest quality value as a primary alignment for the obtained nucleic acid sequence read.

20. A computer implemented method for nucleic acid sequence assembly, the method comprising:
obtaining a nucleic acid sequence read;
obtaining a reference genome;
iteratively selecting anchor sequences comprising differing lengths of a contiguous portion of the nucleic acid sequence read, wherein each anchor sequence begins at a same location on the nucleic acid sequence read;
mapping, using a processor, the anchor sequence to the reference genome using an approximate string mapping method that allows for a set number of mismatches with the reference genome and produces at least one match with the reference genome, wherein the iteratively selecting and mapping of the anchor sequence is performed until a number of matches of the iteratively selected contiguous portion to the reference genome is less than a threshold number;
mapping, using the processor, a remaining portion of the nucleic acid sequence read to the reference genome using an ungapped local alignment method that produces an alignment of the remaining portion extending from the at least one match to map the nucleic acid sequence read to the reference genome;
generating a binary file that stores the mapping of the anchor sequence and remaining portion to the reference genome;

extracting, from the binary file, one or more alignments for the nucleic acid sequence reads from the mapping of the anchor sequence and remaining portion to the reference genome;
calculating alignment scores for the one or more alignments extracted from the binary file, wherein the alignment score represents a quality of the alignment;
classifying a portion of the one or more alignments as duplicates based on the alignment scores; and
marking, in the binary file, the portion of the one or more alignments as duplicates to assemble a nucleotide sequence based on the nucleotide sequence read.

* * * * *